(12) United States Patent
Holtcamp et al.

(10) Patent No.: US 6,858,689 B2
(45) Date of Patent: Feb. 22, 2005

(54) POLYMERIZATION CATALYST ACTIVATORS, METHOD OF PREPARING, AND THEIR USE IN POLYMERIZATION PROCESSES

(75) Inventors: Matthew W. Holtcamp, Huffman, TX (US); David Arthur Cano, Spring, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 10/734,871

(22) Filed: Dec. 12, 2003

(65) Prior Publication Data

US 2004/0167016 A1 Aug. 26, 2004

Related U.S. Application Data

(62) Division of application No. 10/186,361, filed on Jun. 28, 2002, now Pat. No. 6,703,338.

(51) Int. Cl.[7] .............................. C08F 4/64; C08F 4/602
(52) U.S. Cl. ....................... 526/163; 526/160; 526/165; 526/943
(58) Field of Search ................................ 526/160, 163, 526/165, 943

(56) References Cited

U.S. PATENT DOCUMENTS

| | | | |
|---|---|---|---|
| 3,240,770 A | 3/1966 | de Maldé et al. | 260/88.2 |
| 4,434,313 A | 2/1984 | Langer, Jr. | 585/527 |
| 6,147,173 A | 11/2000 | Holtcamp | 526/133 |
| 6,211,105 B1 | 4/2001 | Holtcamp | 502/103 |
| 6,462,156 B2 | 10/2002 | LaPointe | 526/165 |
| 2001/0025115 A1 | 9/2001 | Campbell, Jr. et al. | 556/7 |

FOREIGN PATENT DOCUMENTS

| | | |
|---|---|---|
| EP | 0015763 A1 | 9/1980 |
| EP | 0155682 A2 | 9/1985 |
| EP | 0568151 A2 | 11/1993 |
| JP | 11-80224 | 3/1999 |
| WO | WO 97/17379 | 5/1997 |
| WO | WO 99/42467 | 8/1999 |
| WO | WO 99/64476 | 12/1999 |
| WO | WO 00/20426 | 4/2000 |
| WO | WO 00/29454 | 5/2000 |
| WO | WO 00/35973 | 6/2000 |
| WO | WO 01/09207 | 2/2001 |
| WO | WO 01/23442 | 4/2001 |
| WO | WO 01/38270 | 5/2001 |
| WO | WO 01/62764 | 8/2001 |
| WO | WO 01/83447 | 11/2001 |
| WO | WO 02/08303 | 1/2002 |
| WO | WO 02/074779 | 9/2002 |
| WO | WO 02/102811 | 12/2002 |
| WO | WO 02/102863 | 12/2002 |
| WO | WO 03/064433 | 8/2003 |

OTHER PUBLICATIONS

Langer, Arthur W. et al., "*Supported Catalysts for Polypropylene: Aluminum Alkyl–ester Chemistry,*" Polymer Science and Technology (Plenum), 19(Coord. Polym.), 225–48, (1983).

Abstract: Suzuki, Kazuo et al., "*Polymerization of .alpha.–olefins*" retrieved from STN Database accession no. 92:7197 abstract & JP54021391B (Kanegafuchi Chemical Industry Co., LTD., Japan) Jul. 30, 1979.

Péron, Guillaume L. N. et al, "*Syndio–rich poly(methyl methacrylate) from the anionic polymerisation of methyl methacrylate in the presence of novel organolauminium amides*" J. Mater. Chem, 11, 2915–2918 (2001).

Abstract: Doi, Yasushi: "*Catalyst for olefin polymerization*" retrieved from STN Database accession no. 130:282491, abstract & JP 11080224 (Mitsui Chemicals Inc., Japan) Mar. 26, 1999.

Abstract: Zheng, Ronghui et al, "*Modification effect of electron donors on supported catalyst for propylene polymerization*" retrieved from STN Database accession no. 108:38484 ((Shiyou Huagong, (1987), 16(10), 686–91)).

Abstract: Kamaishi, Tadami et al: "*Catalyst for polymerization of .alpha.–olefins*" retrieved from STN Database accession no. 73:4358 abstract & JP44027734B (Toyo Rayon Co., Ltd.) Nov. 17, 1969.

Abstract: Kamaishi, Tadami et al: "*Polymerization of .alpha.–olefin*" retrieved from STN Database accession no. 71:92059 abstract & JP44013148B (Toyo Rayon Co., Ltd.) Jun. 12, 1969.

Abstract: Kamaishi, Tadami et al: "*Crystalline polyolefins*" retrieved from STN Database accession no. 71:22482, abstract & JP44006828B (Toyo Rayon Co., Ltd.) Mar. 25, 1969.

Abstract: Kamaishi, Tadami et al: "*Polypropylene*" retrieved from STN Database accession no. 70:88432, abstract & JP43029756B (Toyo Rayon Co., Ltd.) Dec. 20, 1968.

Abstract: Kamaishi, Tadami et al: "*Polymerization of .alpha.–olefin*" retrieved from STN Database accession no. 70:68876, abstract & JP43018907B (Toyo Rayon Co., Ltd.) Aug. 16, 1968.

LaPointe, Robert. E, et al: "*New Family of Weakly Coordinating Anions*", J. Am. Chem. Soc 122, 39, 9560–9561, (2000).

(List continued on next page.)

*Primary Examiner*—Caixia Lu
(74) *Attorney, Agent, or Firm*—Kevin M. Faulkner

(57) ABSTRACT

New polymerization catalyst activators are disclosed which include a heterocyclic compound, which may or may not be substituted, and an aluminum alkyl or an aluminoxane. Supported activators of the invention include the heterocyclic compound, combined with an alkylaluminum or aluminoxane, and a support material, preferably a silica support material. Also disclosed are methods for preparing these catalyst activators and polymerization processes utilizing same.

43 Claims, No Drawings

OTHER PUBLICATIONS

Kehr, Gerald et al: "(N–pyrrolyl)B(C$_6$F$_5$)$_2$–A New Organometallic Lewis Acid for the Generation of Group 4 Metallocene Cation Complexes", Chem. Eur. J. 6(2), 258–266, (2000).

Kehr, Gerald et al: "Protonation of the Heterocyclic Cp–Anion Equivalent [Pyrrolyl–B(C$_6$F$_5$)$_3$]Li–Formation of a Useful Neutral Brønsted Acid for the Generation of Homogeneous Metallocene Ziegler Catalysts", Eur. J. Inorg. Chem. 2, 535–538, (2001).

Abstract: Atarashi, Yuji et al: "Catalysts for .alpha.–olefin polymerization" retrieved from STN Database accession no. 67:64854, abstract & JP42006269B (Toyo Rayon Co., Ltd.) Mar. 14, 1967.

R. E. LaPointe, et al., *New Family of Weakly Coordinating Anions*, J. Am. Chem. Soc., 122, 9560–9561 (2000).

G. Kehr, et al., *(N–Pyrrolyl)B(C$_6$F$_5$)$_2$—A New Organometallic Lewis Acid for the Generation of Group 4 Metallocene Cation Complexes*, Chem. Eur. J. 6, No. 2, 258–266 (2000).

POLYMERIZATION CATALYST ACTIVATORS, METHOD OF PREPARING, AND THEIR USE IN POLYMERIZATION PROCESSES

CROSS-REFERENCE TO RELATED APPLICATION

The present application is a Divisional Application of, and claims priority to U.S. Ser. No. 10/186,361 filed Jun. 28, 2002, now issued as U.S. Pat. No. 6,703,338.

FIELD OF THE INVENTION

The present invention relates to polymerization catalyst activator compounds, to methods of making these activator compounds, to polymerization catalyst systems containing these activator compounds, and to polymerization processes utilizing the same. More specifically the activators of the invention include a heterocyclic compound, which may or may not be substituted, and an aluminum alkyl or an aluminoxane. Supported activators of the invention include a heterocyclic compound, which may or may not be substituted, combined with an alkylaluminum or aluminoxane, and a support material, preferably a silica support material.

BACKGROUND OF THE INVENTION

Polymerization catalyst compounds are typically combined with an activator (or co-catalyst) to yield compositions having a vacant coordination site that will coordinate, insert, and polymerize olefins. Metallocene polymerization catalysts are typically activated with aluminoxanes which are generally oligomeric compounds containing —Al(R)—O— subunits, where R is an alkyl group. The most common alumoxane activator is methylalumoxane (MAO), produced by the hydrolysis of trimethylaluminum (TMA). MAO, however, is expensive to utilize because it must be present in great excess relative to the metallocene and because of the high cost of TMA. In addition, MAO tends to be unstable as it precipitates out of solution over time.

In addition, metallocene polymerization catalyst systems, utilized in industrial slurry or gas phases processes, are typically immobilized on a carrier or support, for example silica or alumina. Metallocenes are supported to enhance the morphology of the forming polymeric particles such that they achieve a shape and density that improves reactor operability and ease of handling. Metallocene catalysts, however, typically exhibit lower activity when supported when compared to the corresponding non-supported catalyst systems.

Alternative activators for metallocenes and other single-site polymerization catalysts have been discovered in recent years. For example, perfluorophenyl aluminum and borane complexes containing one anionic nitrogen containing group may activate metallocenes. For example, R. E. LaPointe, G. R. Roof, K. A. Abboud, J. Klosin, J. Am. Chem. Soc. 2000, 122, 9560–9561, and WO 01/23442 A1 report the synthesis of (C6F5)3Al(imidazole)Al(C6F5)3][HNR'R"]. In addition, G. Kehr, R. Fröhlich, B. Wibbeling, G. Erker, Chem. Eur. J. 2000, 6, No.2, 258–266 report the synthesis of (N-Pyrrolyl)B(C6F5)2.

U.S. Pat. Nos. 6,147,173 and 6,211,105 disclose a polymerization process and polymerization catalyst where the catalyst includes an activator complex having a Group 13 element and at least one halogenated, nitrogen-containing aromatic group ligand.

In light of the high cost and low stability of MAO and of the reduced activity when metallocenes are supported, there is a need in the art for new inexpensive, stable and supportable polymerization catalyst activator compounds. There is also a need in the art for methods for preparing these activator compounds, polymerization catalyst systems including these activator compounds and for polymerization processes utilizing the same.

SUMMARY OF THE INVENTION

The activator compounds of the invention, in one embodiment, include a heterocyclic compound, which may or may not be substituted, utilized in combination with an alkylaluminum or aluminoxane and optionally a support material, preferably silica.

In another embodiment, the activator of the invention includes a heterocyclic compound having one or more heteroatoms selected form Group 15 or 16, preferably the heteroatom(s) is nitrogen, oxygen, or sulfur. The heterocyclic compounds may be unsubstituted, or one or more positions may be substituted. In a preferred embodiment, one or more positions on the heterocyclic compound is substituted with a halogen atom or a halogen containing group, where the halogen is chlorine, bromine or fluorine, preferably bromine or fluorine, most preferably fluorine.

In other embodiments, the invention provides for methods of preparing these activator compositions, for utilizing the activators in olefin(s) polymerization processes, and for polymers produced therefrom.

DETAILED DESCRIPTION

The polymerization catalyst activator of the invention includes a heterocyclic compound, which may be unsubstituted or substituted, utilized in combination with an alkylaluminum or an aluminoxane, and an optional support material.

For the purposes of this patent specification, term "activator" is used interchangeably with the term "co-catalyst," the term "catalyst" refers to a metal compound that when combined with an activator polymerizes olefins, and the term "catalyst system" refers to the combination of a catalyst, an activator, and an optional support material.

In one embodiment, the ring of the heterocyclic compound contains at least one atom selected from Group 15 or 16 of the Period Table of the Elements. More preferably the ring of the heterocyclic compound includes at least one nitrogen, oxygen, and/or sulfur atom, and more preferably includes at least one nitrogen atom. Preferably, the heterocyclic compound includes 4 or more ring members and more preferably 5 or more ring members.

The heterocyclic compound may be unsubstituted or substituted with one or a combination of substituent groups. Examples of suitably substituents include hydrogen, halogen, alkyl, alkenyl or alkynyl radicals, cycloalkyl radicals, aryl radicals, aryl substituted alkyl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or any combination thereof. The substituents groups may also be substituted with halogens, particularly fluorine or bromine, or heteroatoms or the like.

Non-limiting examples of substituents include methyl, ethyl, propyl, butyl, pentyl, hexyl, cyclopentyl, cyclohexyl, benzyl or phenyl groups and the like, including all their isomers, for example tertiary butyl, isopropyl, and the like. Other examples of substituents include fluoromethyl, fluoroethyl, difluoroethyl, iodopropyl, bromohexyl or chlorobenzyl.

In one embodiment, the heterocyclic compound is unsubstituted. In another embodiment one or more positions on the heterocyclic compound is substituted with a halogen atom or a halogen atom containing group, for example a halogenated aryl group. Preferably the halogen is chlorine, bromine or fluorine, more preferably fluorine or bromine and even more preferably the halogen is fluorine.

Non-limiting examples of heterocyclic compounds utilized in the activator of the invention include substituted and unsubstituted pyrroles, imidazoles, pyrazoles, pyrrolines, pyrrolidines, purines, carbazoles, and indoles, phenyl indoles, 2,5, dimethyl pyrroles, 3-pentafluorophenyl pyrrole, 4,5,6,7 tetrafluoroindole or 3,4 difluoropyrroles.

In a preferred embodiment, the heterocyclic compound is an indole represented by Formula (I).

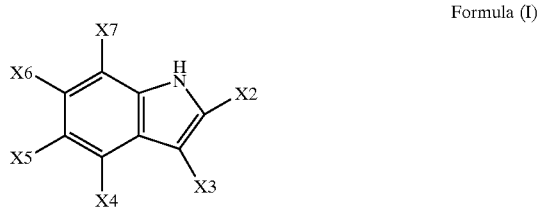

Formula (I)

In Formula I, the indole includes substituent groups X2–X7. Each X2–X7 is independently selected from hydrogen, halogen, preferably chlorine, bromine or fluorine, more preferably bromine or fluorine and most preferably fluorine, an alkyl group, an aryl group, an alkoxide group, an aryloxide group or an alkyl substituted aryl group wherein the groups may be halogenated or partially halogenated, preferably containing a fluorine atom and/or a bromine atom. In one embodiment, the indole is not perhalogenated. Preferably, Each X2–X7 is independently hydrogen, halogen, an alkyl group, a halogenated or partially halogenated alkyl group, an aryl group, a halogenated or partially halogenated aryl group, an aryl substituted alkyl group or a halogenated or partially halogenated aryl substituted alkyl group. Preferably the halogen is chlorine, bromine or fluorine, more preferably bromine or fluorine, and most preferably fluorine. In another embodiment, each of X2–X7 are independently hydrogen or halogen, preferably bromine or fluorine, more preferably fluorine. In another embodiment each of X2–X7 are independently an alkyl group, a halogenated or partially halogenated alkyl group, an aryl group, or a halogenated or partially halogenated aryl group.

In one embodiment, the heterocyclic compound described above are combined with an alkyl aluminum or an alumoxane to yield an activator compound which upon reaction with a catalyst precursor compound, for example a metallocene, produces an active polymerization catalyst.

In one embodiment, the heterocyclic compounds described above are utilized in combination with an alkylaluminum represented by Formula (II).

AlR₃              Formula (II)

wherein each R is independently a substituted or unsubstituted alkyl group and/or a substituted or unsubstituted aryl group. Preferably R is an alkyl group containing 1 to 30 carbon atoms.

Non-limiting examples of alkylaluminums include trimethylaluminum, triethylaluminum, triisobutylaluminum, tri-n-hexylaluminum, tri-n-octylaluminum, tri-isooctylaluminum, triphenylaluminum, and combinations thereof.

In another embodiment, the heterocyclic compounds described above are utilized with an alumoxanes which are generally oligomeric compounds containing —Al(R)—O— or —Al(R)₂—O— subunits, where R is an alkyl group. Examples of alumoxanes include methylalumoxane (MAO), modified methylalumoxane (MMAO), ethylalumoxane, isobutylalumoxane, tetraethyldialumoxane and di-isobutylalumoxane. Alumoxanes may be produced by the hydrolysis of the respective trialkylaluminum compound. MMAO may be produced by the hydrolysis of trimethylaluminum and a higher trialkylaluminum such as triisobutylaluminum. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are fully incorporated herein by reference.

In one embodiment, the activators of the invention are represented by Formula (IIIa) or (IIIb)

$(R'_xM(JY)_y)_n$            Formula (IIIa)

or $[((JY)_yR'_x)_nM—O—M((R'_x(JY)_y)_n]_m$        Formula (IIIb)

or $(OMR'_x(JY)_y)_n$            Formula (IIIc)

In Formulae (IIIa), (IIIb) and (IIIc), M is a Group 13 atom, preferably boron or aluminum, and more preferably aluminum. (JY) represents a heterocyclic group attached to M. In (JY) the Y represents the heterocyclic group as a whole and J represents at least one heteroatom contained in group Y. M may be bonded to any atom contained in Y, but is preferably bonded to heteroatom J.

Preferably, J is an atom selected from Group 15 or 16 of the Period Table of the Elements, more preferably J is nitrogen, oxygen, or sulfur and most preferably J is nitrogen.

Non-limiting examples of (JY) include pyrrolyl, imidazolyl, pyrazolyl, pyrrolidinyl, purinyl, carbazolyl, and indolyl groups.

Heterocyclic group (JY) may be unsubstituted or substituted with one or a combination of substituent groups. Examples of suitably substituents include hydrogen, halogen, linear or branched alkyl, alkenyl or alkynyl radicals, cycloalkyl radicals, aryl radicals, aryl substituted alkyl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. The substituent groups may also be substituted with halogens, particularly fluorine, or heteroatoms or the like.

Non-limiting examples of substituents include methyl, ethyl, propyl, butyl, pentyl, hexyl, cyclopentyl, cyclohexyl, benzyl or phenyl groups and the like, including all their isomers, for example tertiary butyl, isopropyl, and the like. Other examples of substituents include fluoromethyl, fluroethyl, difluroethyl, iodopropyl, bromohexyl, chlorobenzyl.

Preferably one or more positions on the heterocyclic group (JY) is substituted with a halogen atom or a halogen atom containing group, preferably the halogen is chlorine, bromine or fluorine, more preferably bromine or fluorine, and most preferably fluorine. Even more preferably, the substituent is a fluorine atom or a fluorinated aryl group such as a fluorinated phenyl group.

In Formula (IIIa) n is 1 or 2. In Formula (IIIb) n is 2. In Formula (IIIc) n is a number from 1 to 1000 preferably 1 to 100, more preferably 5 to 50, and even more preferably 5–25.

m is a number from 1 to 10.

x+y=the valence of M in Formula (IIIa). x+y=the valence of M-1 in Formulae (IIIb). x+y=valence of M-2 in Formula (IIIc).

Each R' is independently a substituent group bonded to M. Non-limiting examples of substituent R' groups include hydrogen, linear or branched alkyl or alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic alkylene radicals, or combination thereof.

Each R' may be a methyl, ethyl, propyl, butyl, pentyl, hexyl, cyclopentyl, cyclohexyl, benzyl or phenyl group, including all their isomers, for example tertiary butyl, isopropyl, and the like. Other suitable substituents R' include hydrocarbyl radicals such as fluoromethyl, fluoroethyl, difluoroethyl, iodopropyl, bromohexyl, chlorobenzyl; hydrocarbyl substituted organometalloid radicals including trimethylsilyl, trimethylgermyl, methyldiethylsilyl and the like; halocarbyl-substituted organometalloid radicals including tris(trifluoromethyl)-silyl, methyl-bis(difluoromethyl) silyl, bromomethyldimethylgermyl and the like; disubstituted boron radicals including dimethylboron for example; disubstituted pnictogen radicals including dimethylamine, dimethylphosphine, diphenylamine, methylphenylphosphine; and chalcogen radicals including methoxy, ethoxy, propoxy, phenoxy, methylsulfide and ethylsulfide.

Other substituents R' include the atoms carbon, silicon, boron, aluminum, nitrogen, phosphorous, oxygen, tin, sulfur, or germanium and the like. Substituent R' groups also include olefins such as but not limited to olefinically unsaturated substituents including vinyl-terminated ligands, for example but-3-enyl, prop-2-enyl, hex-5-enyl and the like. Also, at least two R groups, preferably two adjacent R' groups, may be joined to form a ring structure having from 3 to 30 atoms selected from carbon, nitrogen, oxygen, phosphorous, silicon, germanium, aluminum, boron or a combination thereof. Also, a substituent group R' such as 1-butanyl may form a carbon sigma bond to the metal M.

In one embodiment, each R' a substituted or unsubstituted alkyl group and/or a substituted or unsubstituted aryl group, and preferably each R' is an alkyl group containing 1 to 30 carbon atoms.

In one embodiment, In Formulae (IIIa), (IIIb) or (IIIc) M is Al or B, preferably Al, J is a nitrogen atom contained in heterocyclic group Y and preferably (JY) is an substituted or unsubstituted indolyl group where the substituents are preferably hydrogen, halogen, an alkyl group, a halogenated or partially halogenated alkyl group, and aryl group, a halogenated or partially halogenated aryl group, an aryl substituted alkyl group, a halogenated or partially halogenated aryl substituted alkyl group, or combinations thereof, preferably J is bound to M, and R' a substituted or unsubstituted alkyl group and/or a substituted or unsubstituted aryl group, preferably an alkyl group containing 1 to 30 carbon atoms.

In another embodiment, in Formulae (IIIa), (IIIb) or (IIIc) M is Al or B, preferably Al, J is a nitrogen atom bonded to M and contained in a heterocyclic group Y where the heterocyclic ligand (JY) is an unsubstituted heterocyclic group. In another embodiment, one or more positions on the heterocyclic group is substituted with a chlorine, bromine and/or fluorine atoms or with chlorine bromine and/or fluorine atom containing groups, more preferably with fluorine atoms or fluorine atom containing groups and R' a substituted or unsubstituted alkyl group and/or a substituted or unsubstituted aryl group, preferably an alkyl group containing 1 to 30 carbon atoms. In another embodiment, (JY) is not a perhalogenated group.

In another embodiment, in Formulae (IIIa), (IIIb) or (IIIc) M is Al or B, preferably Al, J is a nitrogen atom bonded to M and contained in a heterocyclic group Y where the heterocyclic ligand (JY) is an unsubstituted heterocyclic group. In another embodiment, one or more positions on the heterocyclic group is substituted with a halogen such as chlorine bromine and/or fluorine atoms or with a halogen atom, such as a chlorine, bromine and/or fluorine containing groups. More preferably the heterocyclic group is substituted with fluorine atoms or fluorine atom containing groups. In another embodiment, at least one R' is bonded to a support material, preferably a silica support material.

In another embodiment, one or more of the activators of the invention may be used in combination with each other or in combination with other activators or methods of activation. For example, the activators of the invention may be used in combination with other activators including aluminoxane, modified aluminoxane, tri (n-butyl) ammonium tetrakis (pentafluorophenyl) boron, a trisperfluorophenyl boron metalloid precursor or a trisperfluoronapthyl boron metalloid precursor, polyhalogenated heteroborane anions, trimethylaluminum, triethylaluminum, triisobutylaluminum, tri-n-hexylaluminum, tri-n-octylaluminum, tris (2, 2', 2"-nona-fluorobiphenyl) fluoroaluminate, perchlorates, periodates, iodates and hydrates, (2,2'-bisphenyl-ditrimethylsilicate).4THF and organo-boron-aluminum compound, silylium salts and dioctadecylmethylammonium-bis(tris(pentafluorophenyl) borane)-benzimidazolide or combinations thereof.

Catalyst Compositions

The activator of the invention may be utilized in conjunction with any suitable polymerization catalyst compound or compounds to polymerize olefin(s). Examples of suitable catalyst compounds include bulky ligand metallocene catalyst compositions, Group 15 atom containing metal polymerization catalyst compositions, and phenoxide transition metal catalyst compositions. The following is a non-limiting discussion of the various polymerization catalysts which may be utilized with the activators of the invention.

Bulky Ligand Metallocene Catalyst Compositions

The activator complexes of the present invention may be used to activate bulky ligand metallocene catalyst compositions. Generally, these catalyst compounds include half and full sandwich compounds having one or more bulky ligands bonded to at least one metal atom. Typical bulky ligand metallocene compounds are described as containing one or more bulky ligand(s) and one or more leaving group(s) bonded to at least one metal atom.

The bulky ligands may be open, acyclic, fused ring(s) or ring system(s), or a combination thereof. The ring(s) or ring system(s) of these bulky ligands are typically composed of atoms selected from Groups 13 to 16 atoms of the Periodic Table of the Elements. Preferably the atoms are selected from the group consisting of carbon, nitrogen, oxygen, silicon, sulfur, phosphorous, germanium, boron and aluminum or a combination thereof. Most preferably the ring(s) or ring system(s) are composed of carbon atoms such as but not limited to those cyclopentadienyl ligands or cyclopentadienyl-type ligand structures. The bulky ligands may also be other similar functioning ligand structure such as a pentadiene, a cyclooctatetradienyl or an imide ligand. The metal atom is preferably selected from Groups 3 through 15 and the lanthanide or actinide series of the Periodic Table of the Elements. Preferably the metal is a transition metal from Groups 4 through 12, more preferably Groups 4, 5 and 6, and most preferably the transition metal is from Group 4, especially Ti or Zr or Hf.

In one embodiment, the bulky ligand metallocene catalyst compounds, which may be utilized with the activator complex of the invention, may be represented by Formula (IV):

$$L^A L^B M Q_n \qquad \text{Formula (IV)}$$

where M is a metal atom from the Periodic Table of the Elements and may be a Group 3 to 12 metal or from the lanthanide or actinide series of the Periodic Table of the Elements, preferably M is a Group 4, 5 or 6 transition metal, more preferably M is zirconium, hafnium or titanium. The bulky ligands, $L^A$ and $L^B$, are open, acyclic or fused ring(s) or ring system(s) and are any ancillary ligand system, including unsubstituted or substituted, cyclopentadienyl ligands or cyclopentadienyl-type ligands, heteroatom substituted and/or heteroatom containing cyclopentadienyl-type ligands. Non-limiting examples of bulky ligands include cyclopentadienyl ligands, cyclopentaphenanthreneyl ligands, indenyl ligands, benzindenyl ligands, fluorenyl ligands, octahydrofluorenyl ligands, cyclooctatetraendiyl ligands, cyclopentacyclododecene ligands, azenyl ligands, azulene ligands, pentalene ligands, phosphoyl ligands, phosphinimine (WO 99/40125), pyrrolyl ligands, pyrozolyl ligands, carbazolyl ligands, borabenzene ligands and the like, including hydrogenated versions thereof, for example tetrahydroindenyl ligands. In another embodiment, $L^A$ and $L^B$ may comprise one or more heteroatoms, for example, nitrogen, silicon, boron, germanium, sulfur and phosphorous, in combination with carbon atoms to form an open, acyclic, or preferably a fused, ring or ring system, for example, a hetero-cyclopentadienyl ancillary ligand. Other $L^A$ and $L^B$ bulky ligands include but are not limited to bulky amides, phosphides, alkoxides, aryloxides, imides, carbolides, borollides, porphyrins, phthalocyanines, corrins and other polyazomacrocycles. Independently, each $L^A$ and $L^B$ may be the same or different type of bulky ligand that is bonded to M. In one embodiment of Formula (IV) only one of either $L^A$ or $L^B$ is present.

Independently, each $L^A$ and $L^B$ may be unsubstituted or substituted with a combination of substituent groups R. Non-limiting examples of substituent groups R include one or more from the group selected from hydrogen, or linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. In a preferred embodiment, substituent groups R have up to 50 non-hydrogen atoms, preferably from 1 to 30 carbon, that can also be substituted with halogens or heteroatoms or the like. Non-limiting examples of alkyl substituents R include methyl, ethyl, propyl, butyl, pentyl, hexyl, cyclopentyl, cyclohexyl, benzyl or phenyl groups and the like, including all their isomers, for example tertiary butyl, isopropyl, and the like. Other hydrocarbyl radicals include fluoromethyl, fluroethyl, difluroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)-silyl, methyl-bis(difluoromethyl)silyl, bromomethyldimethylgermyl and the like; and disubstituted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents R include the atoms carbon, silicon, boron, aluminum, nitrogen, phosphorous, oxygen, tin, sulfur, germanium and the like, including olefins such as but not limited to olefinically unsaturated substituents including vinyl-terminated ligands, for example but-3-enyl, prop-2-enyl, hex-5-enyl and the like. Also, at least two R groups, preferably two adjacent R groups, are joined to form a ring structure having from 3 to 30 atoms selected from carbon, nitrogen, oxygen, phosphorous, silicon, germanium, aluminum, boron or a combination thereof. Also, a substituent group R group such as 1-butanyl may form a carbon sigma bond to the metal M.

Other ligands may be bonded to the metal M, such as at least one leaving group Q. For the purposes of this patent specification and appended claims the term "leaving group" is any ligand that can be abstracted from a bulky ligand metallocene catalyst compound to form a bulky ligand metallocene catalyst cation capable of polymerizing one or more olefin(s). In one embodiment, Q is a monoanionic labile ligand having a sigma-bond to M. Depending on the oxidation state of the metal, the value for n is 0, 1 or 2 or such that Formula (IV) above represents a neutral bulky ligand metallocene catalyst compound.

Non-limiting examples of Q ligands include weak bases such as amines, phosphines, ethers, carboxylates, dienes, hydrocarbyl radicals having from 1 to 20 carbon atoms, hydrides or halogens and the like or a combination thereof. In another embodiment, two or more Q's form a part of a fused ring or ring system. Other examples of Q ligands include those substituents for R as described above and including cyclobutyl, cyclohexyl, heptyl, tolyl, trifluromethyl, tetramethylene, pentamethylene, methylidene, methyoxy, ethyoxy, propoxy, phenoxy, bis(N-methylanilide), dimethylamide, dimethylphosphide radicals and the like.

In another embodiment, the activator complex of the invention is utilized with the bulky ligand metallocene catalyst compounds of Formula (V) where $L^A$ and $L^B$ are bridged to each other by at least one bridging group, A, as represented in the following formula:

$$L^A A L^B M Q_n \qquad \text{Formula (V)}$$

These bridged compounds represented by Formula (V) are known as bridged, bulky ligand metallocene catalyst compounds. $L^A$, $L^B$, M, Q and n are as defined above. Non-limiting examples of bridging group A include bridging groups containing at least one Group 13 to 16 atom, often referred to as a divalent moiety such as but not limited to at least one of a carbon, oxygen, nitrogen, silicon, aluminum, boron, germanium and tin atom or a combination thereof. Preferably bridging group A contains a carbon, silicon or germanium atom, most preferably A contains at least one silicon atom or at least one carbon atom. The bridging group A may also contain substituent groups R as defined above including halogens and iron. Non-limiting examples of bridging group A may be represented by R'$_2$C, R'$_2$Si, R'$_2$Si R'$_2$Si, R'$_2$Ge, R'P, where R' is independently, a radical group which is hydride, hydrocarbyl, substituted hydrocarbyl, halocarbyl, substituted halocarbyl, hydrocarbyl-substituted organometalloid, halocarbyl-substituted organometalloid, disubstituted boron, disubstituted pnictogen, substituted chalcogen, or halogen or two or more R' may be joined to form a ring or ring system. In one embodiment, the bridged, bulky ligand metallocene catalyst compounds of Formula (V) have two or more bridging groups A (EP 664 301 B1).

In another embodiment, the activator complex of the invention may be utilized with bulky ligand metallocene catalyst compounds where the R substituents on the bulky ligands $L^A$ and $L^B$ of Formulas (IV) and (V) are substituted with the same or different number of substituents on each of the bulky ligands. In another embodiment, the bulky ligands $L^A$ and $L^B$ of formulas (IV) and (V) are different from each other.

In another embodiment, the activator complex of the invention may be utilized with other bulky ligand metallocene catalyst compounds such as those described in U.S. Pat. Nos. 5,064,802, 5,145,819, 5,149,819, 5,243,001, 5,239,022, 5,276,208, 5,296,434, 5,321,106, 5,329,031, 5,304,614, 5,677,401, 5,723,398, 5,753,578, 5,854,363, 5,856,547 5,858,903, 5,859,158, 5,900,517 and 5,939,503 and PCT publications WO 93/08221, WO 93/08199, WO 95/07140, WO 98/11144, WO 98/41530, WO 98/41529, WO 98/46650, WO 99/02540 and WO 99/14221 and European publications EP-A-0 578 838, EP-A-0 638 595, EP-B-0 513 380, EP-A1-0 816 372, EP-A2-0 839 834, EP-B1-0 632 819, EP-B1-0 748 821 and EP-B1-0 757 996, all of which are fully incorporated herein by reference.

In another embodiment, the activator complex of the invention may be utilized with bulky ligand metallocene catalysts which include bridged heteroatom, mono-bulky ligand metallocene compounds. These types of catalysts and catalyst systems are described in, for example, PCT publication WO 92/00333, WO 94/07928, WO 91/ 04257, WO 94/03506, W096/00244, WO 97/15602 and WO 99/20637 and U.S. Pat. Nos. 5,057,475, 5,096,867, 5,055,438, 5,198, 401, 5,227,440 and 5,264,405 and European publication EP-A-0 420 436, all of which are herein fully incorporated by reference.

In this embodiment, the activator complexes of the invention are utilized with a bulky ligand metallocene catalyst compound represented by Formula (VI):

$L^C$AJMQ$_n$     Formula (VI)

where M is a Group 3 to 12 metal atom or a metal selected from the Group of actinides and lanthanides of the Periodic Table of the Elements, preferably M is a Group 4 to 12 transition metal, and more preferably M is a Group 4, 5 or 6 transition metal, and most preferably M is a Group 4 transition metal in any oxidation state, especially Ti or Zr or Hf, $L^C$ is a substituted or unsubstituted bulky ligand bonded to M; A is bonded to $L^C$ and J; J is a heteroatom ancillary ligand; and A is a bridging group; Q is a univalent anionic ligand; and n is the integer 0,1 or 2. In Formula (VI) above, $L^C$, A and J form a fused ring system.

In an embodiment, $L^C$ of formula (VI) is as defined above for $L^A$, A, M and Q of formula (VI) are as defined above in formula (V).

In Formula (VI) J is a heteroatom containing ligand in which J is an element with a coordination number of three from Group 15 or an element with a coordination number of two from Group 16 of the Periodic Table of the Elements. Preferably J contains a nitrogen, phosphorus, oxygen or sulfur atom with nitrogen being most preferred.

In another embodiment, the activator complex of the invention is utilized with a bulky ligand metallocene catalyst compound which is a complex of a metal, preferably a transition metal, a bulky ligand, preferably a substituted or unsubstituted pi-bonded ligand, and one or more heteroallyl moieties, such as those described in U.S. Pat. Nos. 5,527,752 and 5,747,406 and EP-B1-0 735 057, all of which are herein fully incorporated by reference.

In another embodiment the activator complex of the invention is utilized with a ligand metallocene catalyst compound which may be represented by Formula (VII):

$L^D$MQ$_2$(YZ)X$_n$     Formula (VII)

where M is a Group 3 to 16 metal, preferably a Group 4 to 12 transition metal, and most preferably a Group 4, 5 or 6 transition metal; $L^D$ is a bulky ligand that is bonded to M; each Q is independently bonded to M and Q$_2$(YZ) forms a unicharged polydentate ligand; A or Q is a univalent anionic ligand also bonded to M; X is a univalent anionic group when n is 2 or X is a divalent anionic group when n is 1; n is 1 or2.

In Formula (VII), L and M are as defined above for Formula (IV). Q is as defined above for Formula (IV), preferably Q is selected from the group consisting of —O—, —NR—, —CR$_2$— and —S—; Y is either C or S; Z is selected from the group consisting of —OR, —NR$_2$, —CR$_3$, —SR, —SiR$_3$, —PR$_2$, —H, and substituted or unsubstituted aryl groups, with the proviso that when Q is —NR— then Z is selected from one of the group consisting of —OR, —NR$_2$, —SR, —SiR$_3$, —PR$_2$ and —H; R is selected from a group containing carbon, silicon, nitrogen, oxygen, and/or phosphorus, preferably where R is a hydrocarbon group containing from 1 to 20 carbon atoms, most preferably an alkyl, cycloalkyl, or an aryl group; n is an integer from 1 to 4, preferably 1 or 2; X is a univalent anionic group when n is 2 or X is a divalent anionic group when n is 1; preferably X is a carbamate, carboxylate, or other heteroallyl moiety described by the Q, Y and Z combination.

In another embodiment, the activator complex of the invention is utilized with a bulky ligand metallocene catalyst compounds, which include heterocyclic ligand complexes where the bulky ligands, the ring(s) or ring system(s), include one or more heteroatoms or a combination thereof. Non-limiting examples of heteroatoms include a Group 13 to 16 element, preferably nitrogen, boron, sulfur, oxygen, aluminum, silicon, phosphorous and tin. Examples of these bulky ligand metallocene catalyst compounds are described in WO 96/33202, WO 96/34021, WO 97/17379 and WO 98/22486 and EP-A1-0 874 005 and U.S. Pat. No. 5,637, 660, 5,539,124, 5,554,775, 5,756,611, 5,233,049, 5,744,417, and 5,856,258 all of which are herein incorporated by reference.

In another embodiment, the activator complex of the invention may be utilized with bulky ligand metallocene catalyst compounds, which include complexes known as transition metal catalysts based on bidentate ligands containing pyridine or quinoline moieties, such as those described in U.S. application Ser. No. 09/103,620 filed Jun.

23, 1998, which is herein incorporated by reference. In another embodiment, the bulky ligand metallocene catalyst compounds are those described in PCT publications WO 99/01481 and WO 98/42664, which are fully incorporated herein by reference.

In another embodiment, the activator complex of the invention may be utilized with a bulky ligand metallocene catalyst compounds which may be represented by Formula (VIII):

$$((Z)XA_t(YJ))_qMQ_n \quad \text{Formula (VIII)}$$

where M is a metal selected from Group 3 to 13 or lanthanide and actinide series of the Periodic Table of the Elements; Q is bonded to M and each Q is a monovalent, bivalent, or trivalent anion; X and Y are bonded to M; one or more of X and Y are heteroatoms, preferably both X and Y are heteroatoms; Y is contained in a heterocyclic ring J, where J comprises from 2 to 50 non-hydrogen atoms, preferably 2 to 30 carbon atoms; Z is bonded to X, where Z comprises 1 to 50 non-hydrogen atoms, preferably 1 to 50 carbon atoms, preferably Z is a cyclic group containing 3 to 50 atoms, preferably 3 to 30 carbon atoms; t is 0 or 1; when t is 1, A is a bridging group joined to at least one of X,Y or J, preferably X and J; q is 1 or 2; n is an integer from 1 to 4 depending on the oxidation state of M. In one embodiment, where X is oxygen or sulfur then Z is optional. In another embodiment, where X is nitrogen or phosphorous then Z is present. In an embodiment, Z is preferably an aryl group, more preferably a substituted aryl group.

It is also within the scope of this invention, in one embodiment, that the bulky ligand metallocene catalyst compounds, which may be utilized with the activator complex of the invention include complexes of $Ni^{2+}$ $Pd^{2+}$ described in the articles Johnson, et al., "New Pd(II)- and Ni(II)-Based Catalysts for Polymerization of Ethylene and a-Olefins", J. Am. Chem. Soc. 1995, 117, 6414–6415 and Johnson, et al., "Copolymerization of Ethylene and Propylene with Functionalized Vinyl Monomers by Palladium(II) Catalysts", J. Am. Chem. Soc., 1996, 118, 267–268, and WO 96/23010 published Aug. 1, 1996, WO 99/02472, U.S. Pat. Nos. 5,852,145, 5,866,663 and 5,880,241, which are all herein fully incorporated by reference. These complexes can be either dialkyl ether adducts, or alkylated reaction products of the described dihalide complexes that can be activated to a cationic state by the activators of this invention described below.

Also included as bulky ligand metallocene catalyst are those diimine based ligands of Group 8 to 10 metal compounds disclosed in PCT publications WO 96/23010 and WO 97/48735 and Gibson, et al., Chem. Comm., pp. 849–850 (1998), all of which are herein incorporated by reference.

Other bulky ligand metallocene catalysts, which may be utilized with the activator complex of the invention, are those Group 5 and 6 metal imido complexes described in EP-A2-0 816 384 and U.S. Pat. No. 5,851,945, which is incorporated herein by reference. In addition, bridged bis (amido) catalyst compounds are described in WO 96/27439, which is herein incorporated by reference. Other bulky ligand metallocene catalysts are described as bis(hydroxy aromatic nitrogen ligands) in U.S. Pat. No. 5,852,146, which is incorporated herein by reference. Other metallocene catalysts containing one or more Group 15 atoms include those described in WO 98/46651, which is herein incorporated herein by reference. Still another metallocene bulky ligand metallocene catalysts include those multinuclear bulky ligand metallocene catalysts as described in WO 99/20665, which is incorporated herein by reference.

It is also contemplated that in one embodiment, the bulky ligand metallocene catalysts of the invention described above include their structural or optical or enantiomeric isomers (meso and racemic isomers, for example see U.S. Pat. No. 5,852,143, incorporated herein by reference) and mixtures thereof.

Group 15 Atom Containing Polymerization Catalysts

The activator complexes of the invention may also be utilized with Group 15 atom containing polymerization catalyst compounds. Generally, these catalysts includes a Group 3 to 14 metal atom, preferably a Group 3 to 7, more preferably a Group 4 to 6, and even more preferably a Group 4 metal atom, bound to at least one leaving group and also bound to at least two Group 15 atoms, at least one of which is also bound to a Group 15 or 16 atom through another group.

Preferably, at least one of the Group 15 atoms is also bound to a Group 15 or 16 atom through another group which may be a $C_1$ to $C_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and may optionally be bound to hydrogen, a halogen, a heteroatom or a hydrocarbyl group, or a heteroatom containing group.

Group 15 atom containing metal polymerization catalyst compounds may be represented by Formulae (IX) or (X):

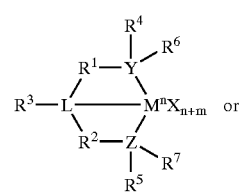

Formula (IX)

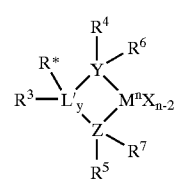

Formula (X)

wherein M is a transition metal, preferably a Group 3 to 14 main group metal, preferably a Group 4, 5, or 6 metal, and more preferably a Group 4 metal, and most preferably zirconium, titanium or hafnium, each X is independently a leaving group, preferably an anionic leaving group, and more preferably hydrogen, a hydrocarbyl group, a heteroatom, or a halogen, and most preferably an alkyl or an aryl substituted alkyl.

y is 0 or 1 (when y is 0 group L' is absent), n is the oxidation state of M, preferably +3, +4, or +5, and more preferably +4, m is the formal charge of the YZL or the YZL' ligand, preferably 0, −1, −2 or −3, and more preferably −2, L is a Group 15 or 16 element, preferably nitrogen, L' is a Group 15 or 16 element or Group 14 containing group, preferably carbon, silicon or germanium, Y is a Group 15 element, preferably nitrogen or phosphorus, and more preferably nitrogen, Z is a Group 15 element, preferably nitrogen or phosphorus, and more preferably nitrogen, $R^1$ and $R^2$ are independently a $C_1$ to $C_{20}$ hydrocarbon group, a heteroatom containing group having up to twenty carbon atoms, silicon, germanium, tin, lead, or phosphorus, preferably a $C_2$ to $C_{20}$ alkyl, aryl or aralkyl group, more preferably a linear, branched or cyclic $C_2$ to $C_{20}$ alkyl group, most preferably a $C_2$ to $C_6$ hydrocarbon group.

$R^3$ is absent, a hydrocarbon group, hydrogen, a halogen, a heteroatom containing group, preferably a linear, cyclic or branched alkyl group having 1 to 20 carbon atoms, more preferably $R^3$ is absent, hydrogen or an alkyl group, and most preferably hydrogen.

$R^4$ and $R^5$ are independently an alkyl group, an aryl group, substituted aryl group, a cyclic alkyl group, a substituted cyclic alkyl group, a cyclic aralkyl group, a substituted cyclic aralkyl group or a multiple ring system, preferably having up to 20 carbon atoms, more preferably between 3 and 10 carbon atoms, and even more preferably a $C_1$ to $C_{20}$ hydrocarbon group, a $C_1$ to $C_{20}$ aryl group or a $C_1$ to $C_{20}$ aralkyl group, or a heteroatom containing group, for example $PR_3$, where R is an alkyl group, $R^1$ and $R^2$ may be interconnected to each other, and/or $R^4$ and $R^5$ may be interconnected to each other, $R^6$ and $R^7$ are independently absent, or hydrogen, an alkyl group, halogen, heteroatom or a hydrocarbyl group, preferably a linear, cyclic or branched alkyl group having 1 to 20 carbon atoms, more preferably absent, and R* is absent, or is hydrogen, a Group 14 atom containing group, a halogen, a heteroatom containing group.

By "formal charge of the YZL or YZL' ligand", it is meant the charge of the entire ligand absent the metal and the leaving groups X. By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups.

Phenoxide Transition Metal Catalyst Compositions

The activator complexes of the invention may also be used with phenoxide transition metal catalyst compounds. Generally, these complexes are heteroatom substituted phenoxide ligated Group 3 to 10 transition metal or lanthanide metal compounds wherein the metal is bound to the oxygen of the phenoxide group.

Phenoxide transition metal catalyst compounds may be represented by Formulae XI or XII:

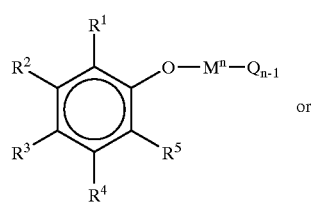

Formula (XI)

or

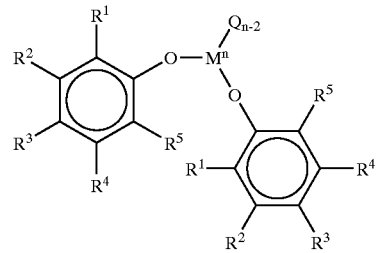

Formula (XII)

wherein $R^1$ is hydrogen or a $C_4$ to $C_{100}$ group, preferably a tertiary alkyl group, preferably a $C_4$ to $C_{20}$ alkyl group, preferably a $C_4$ to $C_{20}$ tertiary alkyl group, preferably a neutral $C_4$ to $C_{100}$ group and may or may not also be bound to M;

at least one of $R^2$ to $R^5$ is a heteroatom containing group, the rest of $R^2$ to $R^5$ are independently hydrogen or a $C_1$ to $C_{100}$ group, preferably a $C_4$ to $C_{20}$ alkyl group, preferred examples of which include butyl, isobutyl, t-butyl, pentyl, hexyl, heptyl, isohexyl, octyl, isooctyl, decyl, nonyl, dodecyl, and any of $R^2$ to $R^5$ also may or may not be bound to M;

Each $R^1$ to $R^5$ group may be independently substituted or unsubstituted with other atoms, including heteroatoms or heteroatom containing group(s);

O is oxygen;

M is a Group 3 to Group 10 transition metal or lanthanide metal, preferably a Group 4 metal, preferably M is Ti, Zr or Hf;

n is the valence state of the metal M, preferably 2, 3, 4, or 5; and

Q is, and each Q may be independently be, an alkyl, halogen, benzyl, amide, carboxylate, carbamate, thiolate, hydride or alkoxide group, or a bond to an R group containing a heteroatom which may be any of $R^1$ to $R^5$.

A heteroatom containing group may be any heteroatom or a heteroatom bound to carbon, silicon or another heteroatom. Preferred heteroatoms include boron, aluminum, silicon, nitrogen, phosphorus, arsenic, tin, lead, antimony, oxygen, selenium, and tellurium. Particularly preferred heteroatoms include nitrogen, oxygen, phosphorus, and sulfur. Even more particularly preferred heteroatoms include nitrogen and oxygen. The heteroatom itself may be directly bound to the phenoxide ring or it may be bound to another atom or atoms that are bound to the phenoxide ring. The heteroatom containing group may contain one or more of the same or different heteroatoms. Preferred heteroatom containing groups include imines, amines, oxides, phosphines, ethers, ketones, oxoazolines heterocyclics, oxazolines, thioethers, and the like. Particularly preferred heteroatom containing groups include imines. Any two adjacent R groups may form a ring structure, preferably a 5 or 6 membered ring. Likewise the R groups may form multi-ring structures. In one embodiment any two or more R groups do not form a 5 membered ring.

In a preferred embodiment the heteroatom substituted phenoxide transition metal compound is an iminophenoxide Group 4 transition metal compound, and more preferably an iminophenoxidezirconium compound.

Other Bulky Ligand Metallocene Catalyst Compounds

Other catalysts are those Group 5 and 6 metal imido complexes described in EP-A2-0 816 384 and U.S. Pat. No. 5,851,945, which is incorporated herein by reference. In addition, other catalysts include bridged bis(arylamido) Group 4 compounds described by D. H. McConville, et al., in Organometallics 1195, 14, 5478–5480, which is herein incorporated by reference. Bridged bis(amido) catalyst compounds are described in WO 96/27439, which is herein incorporated by reference may also be activated by the compositions of the present invention. Other suitable catalysts are described as bis(hydroxy aromatic nitrogen ligands) in U.S. Pat. No. 5,852,146, which is incorporated herein by reference. Other catalysts containing one or more Group 15 atoms include those described in WO 98/46651, which is herein incorporated herein by reference. Still other catalysts include those multinuclear bulky ligand metallocene catalysts as described in WO 99/20665, which is incorporated herein by reference.

It is also contemplated that in one embodiment, the activator complexes of the inventions are utilized with bulky ligand metallocene catalysts including their structural or optical or enantiomeric isomers (meso and racemic isomers, for example see U.S. Pat. No. 5,852,143, incorporated herein by reference) and mixtures thereof.

In another embodiment, it is further contemplated that the polymerization catalysts, described above may be used in combination with the activator(s) of the present invention.

In one embodiment, the mole ratio of the metal of the activator component of the invention to the metal component is preferably in the range of ratios of between 0.3:1 to 3:1.

Supported Catalyst Systems of the Invention

The activator of the invention and/or the polymerization catalyst compound may be combined with one or more support materials or carriers, using one of the support methods known in the art or as described below. For example, in one embodiment the activator is in a supported form, for example deposited on, contacted with, vaporized with, bonded to, or incorporated within, adsorbed or absorbed in, or on, a support or carrier. In another embodiment, the activator and a catalyst compound may be deposited on, contacted with, vaporized with, bonded to, or incorporated within, adsorbed or absorbed in, or on, a support or carrier.

The terms "support" or "carrier", for purposes of this patent specification, are used interchangeably and are any support material, preferably a porous support material, including inorganic or organic support materials. Non-limiting examples of inorganic support materials include inorganic oxides and inorganic chlorides. Other carriers include resinous support materials such as polystyrene, functionalized or crosslinked organic supports, such as polystyrene, divinyl benzene, polyolefins, or polymeric compounds, zeolites, talc, clays, or any other organic or inorganic support material and the like, or mixtures thereof.

In one embodiment, the heterocyclic compounds and the aluminum alkyl and/or the alumoxanes described above are combined with one or more support materials or carriers. In another embodiment the heterocyclic compound is combined with a support material, preferably silica, treated with the alkylaluminum or the alumoxane compound, such that the support has aluminum alkyl groups bonded thereto. The supported catalyst systems of the invention may be prepared, generally, by the reaction of the heterocyclic compound with an aluminum alkyl or aluminoxane, the addition of the catalyst precursor, followed by addition of a support material such as silica or alumina.

The support materials utilized may be any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference. Another support is fumed silica available under the trade name Cabosil™ TS-610, available from Cabot Corporation. Fumed silica is typically a silica with particles 7 to 30 nanometers in size that has been treated with dimethylsilyldichloride such that a majority of the surface hydroxyl groups are capped.

In another embodiment, any of the conventionally known inorganic oxides, such as silica, support materials that retain hydroxyl groups after dehydration treatment methods will be suitable in accordance with the invention. Because of availability, both of silica and silica containing metal oxide based supports, for example, silica-alumina, are preferred. Silica particles, gels and glass beads are most typical.

These metal oxide compositions may additionally contain oxides of other metals, such as those of Al, K, Mg, Na, Si, Ti and Zr and should preferably be treated by thermal and/or chemical means to remove water and free oxygen. Typically such treatment is in a vacuum in a heated oven, in a heated fluidized bed or with dehydrating agents such as organo silanes, siloxanes, alkyl aluminum compounds, etc. The level of treatment should be such that as much retained moisture and oxygen as is possible is removed, but that a chemically significant amount of hydroxyl functionality is retained. Thus calcining at up to 800° C. or more up to a point prior to decomposition of the support material, for several hours is permissible, and if higher loading of supported anionic activator is desired, lower calcining temperatures for lesser times will be suitable. Where the metal oxide is silica, loadings to achieve from less than 0.1 mmol to 3.0 mmol activator/g $SiO_2$ are typically suitable and can be achieved, for example, by varying the temperature of calcining from 200 to 800+° C. See Zhuralev, et al, Langmuir 1987, Vol. 3, 316 where correlation between calcining temperature and times and hydroxyl contents of silicas of varying surface areas is described.

The tailoring of hydroxyl groups available as attachment sites in this invention can also be accomplished by the pre-treatment with a less than stoichimetric amount of a chemical dehydrating agent. If calcining temperatures below 400° C. are employed, difunctional coupling agents (e.g., $(CH_3)_3SiCl_2$) may be employed to cap hydrogen bonded pairs of silanol groups which are present under the less severe calcining conditions. See for example, "Investigation of Quantitative SiOH Determination by the Silane Treatment of Disperse Silica", Gorski, et al, Journ. of Colloid and Interface Science, Vol. 126, No. 2, December 1988, for discussion of the effect of silane coupling agents for silica polymeric fillers that will also be effective for modification of silanol groups on the catalyst supports of this invention. Similarly, use of the Lewis acid in excess of the stoichimetric amount needed for reaction with the transition metal compounds will serve to neutralize excess silanol groups without significant detrimental effect for catalyst preparation or subsequent polymerization.

In another embodiment, the support is a Polymeric support, including hydroxyl-functional-group-containing polymeric substrates, but functional groups may be any of the primary alkyl amines, secondary alkyl amines, and others, where the groups are structurally incorporated in a polymeric chain and capable of a acid-base reaction with the Lewis acid such that a ligand filling one coordination site of the aluminum is protonated and replaced by the polymer incorporated functionality. See, for example, the functional group containing polymers of U.S. Pat. No. 5,288,677.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 μm. More preferably, the surface area of the support material is in the range of from about 50 to about 500 m$^2$/g, pore volume of from about 0.5 to about 3.5 cc/g and average particle size of from about 10 to about 200 μm. The average pore size of the carrier is typically in the range of from 10 to 1000 Å, preferably 50 to about 500 Å, and most preferably 75 to about 350 Å.

The support materials may be treated chemically, for example with a fluoride compound as described in WO 00/12565, which is herein incorporated by reference. Other supported activators are described in for example WO 00/13792 that refers to supported boron containing solid acid complex.

In one embodiment, the support material having an alkylaluminum and/or the alumoxane compound bonded thereto may be prepared by combining the aluminum containing compound with the support material in a suitable solvent. In one embodiment, the combining is carried out at any suitable pressure and temperature under an inert atmosphere. Preferably the combining is at atmospheric pressure, ambient temperature under nitrogen. More preferably the mixture is heated to less than about 200° C., more preferably less than 150° C. The reactants are contacted for a suitable about of time for example, for at least about 1 minute, preferably about 1 minute to about 10 hours, more preferably for about 1 minute to about 3 hours.

Examples of supporting bulky ligand metallocene-type catalyst systems, which may be used to support the activator and/or catalyst systems of the invention are described in U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032, 5,770,664, 5,846,895 and 5,939,348 and U.S. application Ser. Nos. 271,598 filed Jul. 7, 1994 and 788,736 filed Jan. 23, 1997 and PCT publications WO 95/32995, WO 95/14044, WO 96/06187 and WO 97/02297, and EP-B1-0 685 494 all of which are herein fully incorporated by reference.

In another embodiment, an antistatic agent or surface modifier, that is used in the preparation of the supported catalyst system as described in PCT publication WO 96/11960, which is herein fully incorporated by reference, may be used with catalyst systems including the activator compounds of the invention. The catalyst systems of the invention may also be prepared in the presence of an olefin, for example hexene-1.

In another embodiment, activator and/or catalyst system of the invention may be combined with a carboxylic acid salt of a metal ester, for example aluminum carboxylates such as aluminum mono, di- and tri-stearates, aluminum octoates, oleates and cyclohexylbutyrates, as described in U.S. Pat. Nos. 6,300,436 and 6,306,984 incorporated herein by reference.

In another embodiment there is a method for producing a supported bulky ligand metallocene catalyst system, which maybe used to support the activator of the invention which is described below, and is described in U.S. application Ser. Nos. 265,533, filed Jun. 24, 1994 and 265,532, filed Jun. 24, 1994 and PCT publications WO 96/00245 and WO 96/00243 both published Jan. 4, 1996, all of which are herein fully incorporated by reference. In this method, the catalyst compound is slurried in a liquid to form a catalyst solution or emulsion. A separate solution is formed containing the activator. The liquid may be any compatible solvent or other liquid capable of forming a solution or the like with the catalyst compounds and/or activator. In the most preferred embodiment the liquid is a cyclic aliphatic or aromatic hydrocarbon, most preferably toluene. The catalyst compound and activator solutions are mixed together heated and added to a heated porous support or a heated porous support is added to the solutions such that the total volume of the bulky ligand metallocene-type catalyst compound solution and the activator solution or the bulky ligand metallocene-type catalyst compound and activator solution is less than four times the pore volume of the porous support, more preferably less than three times, even more preferably less than two times; preferred ranges being from 1.1 times to 3.5 times range and most preferably in the 1.2 to 3 times range.

In one embodiment, a method of forming a supported catalyst system, the amount of liquid, in which the activator of the invention and/or a catalyst compound is present, is in an amount that is less than four times the pore volume of the support material, more preferably less than three times, even more preferably less than two times; preferred ranges being from 1.1 times to 3.5 times range and most preferably in the 1.2 to 3 times range. In an alternative embodiment, the amount of liquid in which the activator is present is from one to less than one times the pore volume of the support material utilized in forming the supported activator.

Procedures for measuring the total pore volume of a porous support are well known in the art. Details of one of these procedures is discussed in Volume 1, *Experimental Methods in Catalytic Research* (Academic Press, 1968) (specifically see pages 67–96). This preferred procedure involves the use of a classical BET apparatus for nitrogen absorption. Another method well known in the art is described in Innes, *Total Porosity and Particle Density of Fluid Catalysts By Liquid Titration*, Vol. 28, No. 3, Analytical Chemistry 332–334 (March, 1956).

Polymerization Process

The activators of the invention, catalyst systems and supported catalyst systems utilizing the activators described above are suitable for use in any prepolymerization and/or polymerization process over a wide range of temperatures and pressures. The temperatures may be in the range of from −60° C. to about 280° C., preferably from 50° C. to about 200° C. In another embodiment the polymerization temperature is above 0° C., above 50° C., above 80° C., above 100° C., above 150° C., or above 200° C. In one embodiment the pressures employed may be in the range from 1 atmosphere to about 500 atmospheres or higher.

Polymerization processes include solution, gas phase, slurry phase and a high pressure process or a combination thereof. Particularly preferred is a gas phase or slurry phase polymerization of one or more olefin(s) at least one of which is ethylene or propylene.

In one embodiment, the process of the invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, butene-1, pentene-1, 4-methyl-pentene-1, hexene-1, octene-1 and decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In another embodiment of the process of the invention, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In one embodiment, the invention is directed to a polymerization process, particularly a gas phase or slurry phase process, for polymerizing propylene alone or with one or more other monomers including ethylene, and/or other olefins having from 4 to 12 carbon atoms.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.)

The reactor pressure in a gas phase process may vary from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C to about 115° C., more preferably in the range of from about 70° C. to 110° C., and most preferably in the range of from about 70° C. to about 95° C. In another embodiment, the reactor temperature in a gas phase process is above 60° C.

Other gas phase processes contemplated by the process of the invention include series or multistage polymerization processes. Also gas phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-634 421 all of which are herein fully incorporated by reference.

In another embodiment, the reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range of 0° C. to about 120° C. In another embodiment, the slurry process temperature is above 100° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In another embodiment, the polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998 and 5,589,555 and PCT WO 99/32525, which are fully incorporated herein by reference.

In one embodiment of the process of the invention is the process, preferably a slurry or gas phase process is operated in the presence of the catalyst system of the invention and in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. Nos. 5,712,352 and 5,763,543, which are herein fully incorporated by reference.

In another embodiment, the method of the invention provides for injecting the catalyst system of the invention into a reactor, particularly a gas phase reactor. In one embodiment the catalyst system is used in the unsupported form, preferably in a liquid form such as described in U.S. Pat. Nos. 5,317,036 and 5,693,727 and European publication EP-A-0 593 083, all of which are herein incorporated by reference. The polymerization catalyst in liquid form can be fed with an activator, and/or a support, and/or a supported activator together or separately to a reactor. The injection methods described in PCT publication WO 97/46599, which is fully incorporated herein by reference, may be utilized. Where an unsupported catalyst system is used the mole ratio of the metal of the Lewis acid activator component to the metal of the phenoxide transition metal catalyst compound is in the range of between 0.3:1 to 10,000:1, preferably 100:1 to 5000:1, and most preferably 500:1 to 2000:1.

Polymer Products

The polymers produced by the process of the invention can be used in a wide variety of products and end-use applications. The polymers produced include linear low density polyethylene, elastomers, plastomers, high density polyethylenes, medium density polyethylenes, low density polyethylenes, polypropylene and polypropylene copolymers.

The polymers, typically ethylene based polymers, have a density in the range of from 0.86g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. Density is measured in accordance with ASTM-D-1238.

The polymers produced by the process of the invention typically have a molecular weight distribution, a weight average molecular weight to number average molecular weight ($M_w/M_n$) of greater than 1.5 to about 15, particularly greater than 2 to about 10, more preferably greater than about 2.2 to less than about 8, and most preferably from 2.5 to 8.

Also, the polymers of the invention typically have a narrow composition distribution as measured by Composition Distribution Breadth Index (CDBI). Further details of determining the CDBI of a copolymer are known to those skilled in the art. See, for example, PCT Pat. Application WO 93/03093, published Feb. 18, 1993, which is fully incorporated herein by reference. The polymers of the invention in one embodiment have CDBI's generally in the range of greater than 50% to 100%, preferably 99%, preferably in the range of 55% to 85%, and more preferably 60% to 80%, even more preferably greater than 60%, still even more preferably greater than 65%.

In another embodiment, polymers produced using a catalyst system of the invention have a CDBI less than 50%, more preferably less than 40%, and most preferably less than 30%.

The polymers of the present invention in one embodiment have a melt index (MI) or ($I_2$) as measured by ASTM-D-1238-E in the range from no measurable flow to 1000 dg/min, more preferably from about 0.01 dg/min to about 100 dg/min, even more preferably from about 0.1 dg/min to about 50 dg/min, and most preferably from about 0.1 dg/min to about 10 dg/min.

The polymers of the invention in an embodiment have a melt index ratio ($I_{21}/I_2$) ($I_{21}$ is measured by ASTM-D-1238-F) of from 10 to less than 25, more preferably from about 15 to less than 25.

The polymers of the invention in a preferred embodiment have a melt index ratio ($I_{21}/I_2$) ($I_{21}$ is measured by ASTM-D-1238-F) of from preferably greater than 25, more preferably greater than 30, even more preferably greater that 40, still even more preferably greater than 50 and most preferably greater than 65. In an embodiment, the polymer of the invention may have a narrow molecular weight distribution and a broad composition distribution or vice-versa, and may be those polymers described in U.S. Pat. No. 5,798,427 incorporated herein by reference.

In yet another embodiment, propylene based polymers are produced in the process of the invention. These polymers include atactic polypropylene, isotactic polypropylene, hemi-isotactic and syndiotactic polypropylene. Other propylene polymers include propylene block or impact copolymers. Propylene polymers of these types are well known in the art see for example U.S. Pat. Nos. 4,794,096, 3,248,455, 4,376,851, 5,036,034 and 5,459,117, all of which are herein incorporated by reference.

The polymers of the invention may be blended and/or coextruded with any other polymer. Non-limiting examples of other polymers include linear low density polyethylenes, elastomers, plastomers, high pressure low density polyethylene, high density polyethylenes, polypropylenes and the like.

Polymers produced by the process of the invention and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, pipe, geomembranes, and pond liners. Molded articles include single and multi-layered constructions in the form of bottles, tanks, large hollow articles, rigid food containers and toys, etc.

EXAMPLES

In order to provide a better understanding of the present invention including representative advantages thereof, the following examples are offered.

Comparative Example 1

Silica supported (1,3-MeBuCp)$_2$ZrCl$_2$, activated with MAO, was prepared in accordance with the method outlined in U.S. Pat. No. 5,712,352, incorporated herein by reference.

Example 2

0.07 grams of triethylaluminum in toluene were combined with 1.0 grams of silica (Davison 948 calcined at 600° C., 2 wt %F) in a 100 flask. The resulting slurry was allowed to sit overnight. The silica was then filtered, and rinsed with several 10 ml portions of toluene. 0.10 grams of 4,5,6,7-tetrafluoroindole was added to the silica, slurried in toluene and heated to 100° C. for 1.5 hours. The silica was then filtered, rinsed with several 10 ml portions of toluene, and subsequently combined with 0.09 grams of a 20 wt % solution of (1,3-Me,BuCp)$_2$ZrMe$_2$ in toluene. The supported catalyst was allowed to sit at room temperature for 1 hr. The catalyst was filtered, rinsed with several 10 ml portions of toluene, and dried under a vacuum.

Example 3

0.08 grams of triethylaluminum in toluene were combined with 1.0 grams of silica (Davison 948 calcined at 200° C.) in a 100 flask. The resulting slurry was allowed to sit overnight. The silica was then filtered, and rinsed with several 10 ml portions of toluene. 0.10 grams of 4,5,6,7-tetrafluoroindole was added to silica, slurried in toluene and heated to 100° C. for 1.5 hours. The silica was then filtered, rinsed with several 10 ml portions of toluene, and subsequently combined with 0.09 grams of a 20 wt % solution of (1,3-Me,BuCp)$_2$ZrMe$_2$ in toluene. The supported catalyst was allowed to sit at room temperature for 1 hr. The catalyst was filtered, rinsed with several 10 ml portions of toluene, and dried under a vacuum.

Example 4

0.08 grams of triethylaluminum in toluene were combined with 1.0 grams of silica (Davison 948 calcined at 200° C.) in a 100 flask. The resulting slurry was allowed to sit overnight. The resulting silica was filtered, and rinsed with several 10 ml portions of toluene. 0.090 grams of 4,5,6,7-tetrafluoroindole was added to silica, slurried in o-xylene and heated to 140° C. for 1.5 hours. The silica was then filtered, rinsed with several 10 ml portions of toluene, and subsequently combined with 0.09 grams of a 20 wt % solution of (1,3-Me,BuCp)$_2$ZrMe$_2$ in toluene. The supported catalyst was allowed to sit at room temperature for 1 hr. The catalyst was filtered, rinsed with several 10 ml portions of toluene, and dried under a vacuum.

Example 5

In a 100 ml r.b. flask, 200 mg of tetraethylaluminoxane (1.0 M in toluene) was dissolved in 30 ml of toluene. To this solution, 1.00 g. of silica (Davison 948 calcined at 200° C.) was added. This slurry was allowed to stand overnight at room temperature. The slurry was filtered through a frit, washed with toluene (3×10 ml) and partially dried under vacuum. In a dried 100 ml r.b. flask, 400 mg of 4,5,6,7-tetrafluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 135° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution of (1,3-Me,BuCp)$_2$ZrMe$_2$ in toluene was dissolved in 30 ml of toluene. The partially dried silica was transferred into the flask and the slurry was allowed to stand overnight at room temperature. The slurry was filtered through a frit and dried thoroughly under vacuum.

Example 6

In a 100 ml r.b. flask, 200 mg of 4,5,6,7-tetrafluoroindole was dissolved in 30 ml of o-xylene. To this solution, 1.00 g. of TEAL-treated silica (Davison 948 calcined at 600° C.) was added. An immediate, noticeable color change was observed from the off-white silica to a yellow-tinted slurry. The flask was placed in an oil bath at 135° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution of (1,3-Me,BuCp)$_2$ZrMe$_2$ in toluene was dissolved in 30 ml of toluene. The partially dried silica was transferred into the flask and the slurry was allowed to stand overnight at room temperature. The slurry was filtered through a frit and dried thoroughly under vacuum.

Example 7

0.16 grams of triethylaluminum in toluene were combined with 1.0 grams of silica (Davison 948 calcined at 600° C.) in a 100 flask. The resulting slurry was allowed to sit overnight. The resulting silica was filtered, and rinsed with several 10 ml portions of toluene. 0.05 grams of 4,5,6,7-tetrafluoroindole was added to silica, slurried in o-xylene and heated to 140° C. for three hours. Over the three hour period, the color of the slurry darkened to an orange and finally a dark orange/brown hue. The silica was then filtered, rinsed with several 10 ml portions of toluene, and subsequently combined with 0.09 grams of a 20 wt % solution of (1,3-Me,BuCp)$_2$ZrMe$_2$ in toluene. The supported catalyst was allowed to sit at room temperature for 1 hr. The catalyst was filtered, rinsed with several 10 ml portions of toluene, and dried under a vacuum.

Example 8

0.16 grams of triethylaluminum in toluene were combined with 1.0 grams of silica (Davison 948 calcined at 600° C.) in a 100 flask. The resulting slurry was allowed to sit overnight. The resulting silica was filtered, and rinsed with several 10 ml portions of toluene. 0.2 grams of 4,5,6,7-tetrafluoroindole was added to silica, slurried in o-xylene and heated to 140° C. for three hours. The silica was then filtered, rinsed with several 10 ml portions of toluene, and subsequently combined with 0.09 grams of a 20 wt % solution of (1,3-Me,BuCp)$_2$ZrMe$_2$ in toluene. The supported catalyst was allowed to sit at room temperature for 1 hr. The catalyst was filtered, rinsed with several 10 ml portions of toluene, and dried under a vacuum.

Example 9

In a 100 ml r.b. flask, 100 mg of triethylaluminum was dissolved in 30 ml of toluene. To this solution, 1.00 g. of silica (Davison 948 calcined at 300° C.) was added. This slurry was allowed to stand overnight at room temperature. The slurry was filtered through a frit, washed with toluene (3×10 ml) and partially dried under vacuum. In a dried 100 ml r.b. flask, 200 mg of 4,5,6,7-tetrafluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under, vacuum. In a dried 100 ml r.b. flask, 100 mg of of a 20 wt % solution of $(1,3\text{-Me},\text{BuCp})_2\text{ZrMe}_2$ in toluene was dissolved in 30 ml of toluene. The partially dried silica was transferred into the flask and the slurry was allowed to stand overnight at room temperature. The slurry was filtered through a frit and dried thoroughly under vacuum.

Example 10

In a 100 ml r.b. flask, 250 mg of triethylaluminum was dissolved in 30 ml of toluene. To this solution, 1.00 g. of silica (Davison 948 calcined at 200° C.) was added. This slurry was allowed to stand overnight at room temperature. The slurry was filtered through a flit, washed with toluene (3×10 ml) and partially dried under vacuum. In a dried 100 ml r.b. flask, 200 mg of 4,5,6,7-tetrafluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution of $(1,3\text{-Me},\text{BuCp})_2\text{ZrMe}_2$ in toluene was dissolved in 30 ml of toluene. The partially dried silica was transferred into the flask and the slurry was allowed to stand overnight at room temperature. The slurry was filtered through a flit and dried thoroughly under vacuum.

Example 11

In a 100 ml r.b. flask, 250 mg of triethylaluminum was dissolved in 30 ml of toluene. To this solution, 1.00 g. of silica (948 calcined at 300° C.) was added. This slurry was allowed to stand overnight at room temperature. The slurry was filtered through a flit, washed with toluene (3×10 ml) and partially dried under vacuum. In a dried 100 ml r.b. flask, 200 mg of 4,5,6,7-tetrafluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution of $(1,3\text{-Me},\text{BuCp})_2\text{ZrMe}_2$ in toluene was dissolved in 30 ml of toluene. The partially dried silica was transferred into the flask and the slurry was allowed to stand overnight at room temperature. The slurry was filtered through a frit and dried thoroughly under vacuum.

Example 12

0.07 grams of triethylaluminum in toluene were combined with 1.0 grams of silica (Davison 948 600° C.) in a 100 flask. The resulting slurry was allowed to sit overnight. The resulting silica was filtered, and rinsed with several 10 ml portions of toluene. 0.2 grams of 4,5,6,7-tetrafluoroindole was added to silica, slurried in o-xylene and heated to 140° C. for 1.5 hours. Over the 1.5 hour period, the color of the slurry darkened to an orange and finally a dark orange/brown hue. The silica was then filtered, rinsed with several 10 ml portions of toluene, and subsequently combined with 0.09 grams of a 20 wt % solution of $(1,3\text{-Me},\text{BuCp})_2\text{ZrMe}_2$ in toluene. The supported catalyst was allowed to sit at room temperature for 1 hr. The catalyst was filtered, rinsed with several 10 ml portions of toluene, and dried under a vacuum.

Example 13

0.25 grams of triethylaluminum in toluene were combined with 1.0 grams of silica (Davison 948 200° C.) in a 100 flask. The resulting slurry was allowed to sit overnight. The resulting silica was filtered, and rinsed with several 10 ml portions of toluene. 0.1 grams of 4,5,6,7-tetrafluoroindole was added to silica, slurried in o-xylene and heated to 140° C. for three hours. Over the three hour period, the color of the slurry darkened to an orange and finally a dark orange/brown hue. The silica was then filtered, rinsed with several 10 ml portions of toluene, and subsequently combined with 0.09 grams of a 20 wt % solution of $(1,3\text{-Me},\text{BuCp})_2\text{ZrMe}_2$ in toluene. The supported catalyst was allowed to sit at room temperature for 1 hr. The catalyst was filtered, rinsed with several 10 ml portions of toluene, and dried under a vacuum.

Example 14

0.07 grams of triethylaluminum in toluene were combined with 1.0 grams of silica (Davison 948 600° C. , 2 wt %F) in a 100 flask. The resulting slurry was allowed to sit overnight. The resulting silica was filtered, and rinsed with several 10 ml portions of toluene. 0.20 grams of 4,5,6,7-tetrafluoroindole was added to silica, slurried in toluene and heated to 100° C. for 1.5 hours. Over the 1.5 hour period, the color of the slurry darkened to an orange and finally a dark orange/brown hue. The silica was then filtered, rinsed with several 10 ml portions of toluene, and subsequently combined with 0.09 grams of a 20 wt % solution of $(1,3\text{-Me},\text{BuCp})_2\text{ZrMe}_2$ in toluene. The supported catalyst was allowed to sit at room temperature for 1 hr. The catalyst was filtered, rinsed with several 10 ml portions of toluene, and dried under a vacuum.

Example 15

0.07 grams of triethylaluminum in toluene were combined with 1.0 grams of silica (Davison 948 600° C.) in a 100 flask. The resulting slurry was allowed to sit overnight. The resulting silica was filtered, and rinsed with several 10 ml portions of toluene. 0.050 grams of 4,5,6,7-tetrafluoroindole was added to silica, slurried in o-xylene and heated to 140° C. for 1.5 hours. Over the 1.5 hour period, the color of the slurry darkened to an orange and finally a dark orange/brown hue. The silica was then filtered, rinsed with several 10 ml portions of toluene, and subsequently combined with 0.09 grams of a 20 wt % solution of $(1,3\text{-Me},\text{BuCp})_2\text{ZrMe}_2$ in toluene. The supported catalyst was allowed to sit at room temperature for 1 hr. The catalyst was filtered, rinsed with several 10 ml portions of toluene, and dried under a vacuum.

Example 16

In a 100 ml r.b. flask, 200 mg of tetraethylaluminoxane (1.0 M in toluene) was dissolved in 30 ml of toluene. To this solution, 1.00 g. of silica (948 calcined at 300° C.) was added. This slurry was allowed to stand overnight at room temperature. The slurry was filtered through a frit, washed with toluene (3×10 ml) and partially dried under vacuum. In a dried 100 ml r.b. flask, 200 mg of 4,5,6,7-tetrafluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100mg of a 20 wt % solution of (1,3-Me,BuCp)$_2$ZrMe$_2$ in toluene was dissolved in 30 ml of toluene. The partially dried silica was transferred into the flask and the slurry was allowed to stand overnight at room temperature. The slurry was filtered through a frit and dried thoroughly under vacuum.

Polymerizations

Polymerizations utilizing the supported catalyst systems prepared in Examples 1–16 were performed in a glass-lined 20-milliliter autoclave reactor equipped with a mechanical stirrer, an external heater for temperature control, a septum inlet and a regulated supply of dry nitrogen and ethylene in an inert atmosphere (Nitrogen) glove box.

The reactor was dried and degassed thoroughly at 115° C. The diluent, comonomer, and scavenger (if used), were added at room temperature and atmospheric pressure. The reactor was then brought to process pressure and charged with ethylene while stirring at 800 RPM. The activator and catalyst were added via syringe with the reactor at process conditions. The polymerization was continued while maintaining the reaction vessel within 3° C. of the target process temperature and 5 psig of target process pressure (by automatic addition of ethylene on demand) until a fixed uptake of ethylene was noted (corresponding to ca. 0.15 g polymer) or until a maximum reaction time of 40 minutes had passed. The reaction was stopped by pressurizing the reactor to 30 psig above the target process pressure with a gas mixture composed of 5 mol % Oxygen in Argon. The polymer was recovered by vacuum centrifugation of the reaction mixture. Bulk polymerization activity was calculated by dividing the yield of polymer by the total weight of the catalyst charge by the time in hours and by the absolute monomer pressure in atmospheres. The specific polymerization activity was calculated by dividing the yield of polymer by the total number of millimoles of transition metal contained in the catalyst charge by the time in hours and by the absolute monomer pressure in atmospheres. Pertinent data, for the polymers prepared by the catalyst systems of Examples 1–16, is summarized in Table 1.

TABLE 1

Polymerization Data Utilizing Catalyst Systems of Examples 1–16

| Example | | Comonomer Incorporation | Average Mw | Average Mn | Average PDI | Yield g | Activity (gpol./gcat.*hr) |
|---|---|---|---|---|---|---|---|
| Comp. 1 | | 3.2 | 384294.4 | 210524 | 1.8 | 0.126 | 540.4 |
| Comp. 1 | | 3 | 388432.4 | 182978 | 2.1 | 0.121 | 581.4 |
| Comp. 1 | | 2.7 | 387380.3 | 193085 | 2.0 | 0.127 | 588.0 |
| | average | 3.0 | 386702 | 195529 | 2.0 | 0.125 | 569.9 |
| | stddev | 0.3 | 2151 | 13935 | 0.2 | 0.003 | 25.8 |
| 2 | | 2.4 | 488364.2 | 294861 | 1.7 | 0.096 | 213.3 |
| 2 | | 2.5 | 473494.7 | 197664 | 2.4 | 0.106 | 235.5 |
| 2 | | 2.8 | 460380.8 | 200747 | 2.3 | 0.089 | 197.7 |
| | average | 2.6 | 474080 | 231091 | 2.1 | 0.097 | 215.5 |
| | stddev | 0.2 | 14001 | 55249 | 0.4 | 0.009 | 19.0 |
| 3 | | 2.7 | 492415.7 | 279347 | 1.8 | 0.108 | 240.0 |
| 3 | | 2.3 | 497942.3 | 293455 | 1.7 | 0.085 | 188.8 |
| 3 | | 2.5 | 483749.5 | 234490 | 2.1 | 0.097 | 215.5 |
| | average | 2.5 | 491369 | 269097 | 1.9 | 0.097 | 214.8 |
| | stddev | 0.2 | 7154 | 30789 | 0.2 | 0.012 | 25.6 |
| 4 | | 2.4 | 505596.9 | 270467 | 1.9 | 0.071 | 157.7 |
| 4 | | 2.5 | 495952 | 289348 | 1.7 | 0.07 | 155.5 |
| 4 | | 2.5 | 502853.1 | 308021 | 1.6 | 0.068 | 151.1 |
| | average | 2.5 | 501467 | 289279 | 1.7 | 0.070 | 154.8 |
| | stddev | 0.1 | 4970 | 18777 | 0.2 | 0.002 | 3.4 |
| 5 | | 2.6 | 534594.8 | 261170 | 2 | 0.034 | 75.5 |
| 5 | | 2.4 | 529599.8 | 319500 | 1.7 | 0.033 | 73.3 |
| 5 | | 2.4 | 533958.8 | 323033 | 1.7 | 0.033 | 73.3 |
| | average | 2.5 | 532718 | 301234 | 1.8 | 0.033 | 74.1 |
| | stddev | 0.1 | 2719 | 34741 | 0.2 | 0.001 | 1.3 |
| 6 | | 2.4 | 413283.6 | 249554 | 1.7 | 0.126 | 518.7 |
| 6 | | 2.7 | 428413.4 | 250426 | 1.7 | 0.121 | 386.1 |
| 6 | | 2.8 | 427108 | 180713 | 2.4 | 0.118 | 394.8 |
| | average | 2.6 | 422935 | 226898 | 1.9 | 0.122 | 433.2 |
| | stddev | 0.2 | 8384 | 39999 | 0.4 | 0.004 | 74.2 |
| 7 | | 2.6 | 450490 | 253608 | 1.8 | 0.109 | 242.2 |
| 7 | | 2.6 | 473306.2 | 216051 | 2.2 | 0.092 | 204.4 |
| 7 | | 2.7 | 460814.3 | 277469 | 1.7 | 0.104 | 231.0 |
| | average | 2.6 | 461537 | 249043 | 1.9 | 0.102 | 225.9 |
| | stddev | 0.1 | 11425 | 30962 | 0.3 | 0.009 | 19.4 |
| 8 | | 2.7 | 412245.7 | 230767 | 1.8 | 0.12 | 489.4 |
| 8 | | 2.8 | 425803 | 253212 | 1.7 | 0.113 | 452.2 |
| 8 | | 2.9 | 435136.5 | 245094 | 1.8 | 0.124 | 483.5 |

TABLE 1-continued

Polymerization Data Utilizing Catalyst Systems of Examples 1–16

| Example | | Comonomer Incorporation | Average Mw | Average Mn | Average PDI | Yield g | Activity (gpol./gcat.*hr) |
|---|---|---|---|---|---|---|---|
| | average | 2.8 | 424395 | 243024 | 1.8 | 0.119 | 475.1 |
| | stddev | 0.1 | 11510 | 11365 | 0.1 | 0.006 | 20.0 |
| 9 | | 2.6 | 416014.3 | 227484 | 1.8 | 0.118 | 747.5 |
| 9 | | 2.7 | 426636.9 | 256396 | 1.7 | 0.121 | 709.4 |
| 9 | | 2.6 | 412179.3 | 258209 | 1.6 | 0.123 | 635.1 |
| | average | 2.6 | 418277 | 247363 | 1.7 | 0.121 | 697.3 |
| | stddev | 0.1 | 7490 | 17240 | 0.1 | 0.003 | 57.2 |
| 10 | | 3 | 368421.1 | 158260 | 2.3 | 0.136 | 1175.2 |
| 10 | | 3.2 | 368194.5 | 152915 | 2.4 | 0.134 | 1082.2 |
| 10 | | 3.1 | 375514.8 | 208971 | 1.8 | 0.136 | 1091.1 |
| | average | 3.1 | 370710 | 173382 | 2.2 | 0.135 | 1116.1 |
| | stddev | 0.1 | 4163 | 30936 | 0.3 | 0.001 | 51.3 |
| 11 | | 2.9 | 371230.9 | 219215 | 1.7 | 0.134 | 928.9 |
| 11 | | 2.9 | 373737.8 | 178173 | 2.1 | 0.126 | 763.7 |
| 11 | | 2.7 | 384209.4 | 95935.8 | 4 | 0.125 | 697.7 |
| | average | 2.8 | 376393 | 164441 | 2.6 | 0.128 | 796.8 |
| | stddev | 0.1 | 6885 | 62776 | 1.2 | 0.005 | 119.1 |
| 12 | | 2.5 | 452255.5 | 273513 | 1.7 | 0.12 | 312.3 |
| 12 | | 2.4 | 459286.3 | 280637 | 1.6 | 0.118 | 317.4 |
| 12 | | 2.4 | 454071.4 | 253811 | 1.8 | 0.121 | 320.4 |
| | average | 2.4 | 455204 | 269320 | 1.7 | 0.120 | 316.7 |
| | stddev | 0.1 | 3650 | 13896 | 0.1 | 0.002 | 4.1 |
| 13 | | 2.9 | 389071.4 | 224975 | 1.7 | 0.126 | 759.8 |
| 13 | | 2.8 | 407174.1 | 240628 | 1.7 | 0.127 | 769.9 |
| 13 | | 2.7 | 402496.9 | 244037 | 1.6 | 0.125 | 777.9 |
| | average | 2.8 | 399581 | 236547 | 1.7 | 0.126 | 769.2 |
| | stddev | 0.1 | 9397 | 10165 | 0.1 | 0.001 | 9.1 |
| 14 | | 2.6 | 569861.2 | 306875 | 1.9 | 0.03 | 66.6 |
| 14 | | 2 | 604007.1 | 297091 | 2 | 0.028 | 62.2 |
| 14 | | 1.6 | 603578 | 372672 | 1.6 | 0.03 | 66.7 |
| | average | 2.1 | 592482 | 325546 | 1.8 | 0.029 | 65.2 |
| | stddev | 0.5 | 19591 | 41104 | 0.2 | 0.001 | 2.6 |
| 15 | | 2.7 | 498835.6 | 295027 | 1.7 | 0.051 | 113.3 |
| 15 | | 2.4 | 517815.5 | 310117 | 1.7 | 0.049 | 108.9 |
| 15 | | 2.8 | 493251.1 | 251626 | 2 | 0.048 | 106.6 |
| | average | 2.6 | 503301 | 285590 | 1.8 | 0.049 | 109.6 |
| | stddev | 0.2 | 12877 | 30366 | 0.2 | 0.002 | 3.4 |
| 16 | | 2.6 | 449126.6 | 266821 | 1.7 | 0.059 | 131.1 |
| 16 | | 2.8 | 450262.2 | 262548 | 1.7 | 0.058 | 128.9 |
| 16 | | 2.6 | 461867.4 | 278393 | 1.7 | 0.051 | 113.3 |
| | average | 2.7 | 453752 | 269254 | 1.7 | 0.056 | 124.4 |
| | stddev | 0.1 | 7051 | 8198 | 0.0 | 0.004 | 9.7 |

Example 17

10.0 grams of triethylaluminum in toluene were combined with 40.0 grams of silica (Davison 948 200° C.) in a 100 flask. The resulting slurry was allowed to sit overnight. The resulting silica was filtered, and rinsed with several 100 ml portions of toluene. 4.0 grams of 4,5,6,7-tetrafluoroindole was added to silica, slurried in o-xylene and heated to 140° C. for three hours. Over the three hour period, the color of the slurry darkened to an orange and finally a dark orange/brown hue. The silica was then filtered, rinsed with several 100 ml portions of toluene, and dried under vacuum. 36.0 grams of the support was combined with 2.7 grams of a 20 wt % solution of (1,3-Me,BuCp)$_2$ZrMe$_2$ in toluene. The supported catalyst was allowed to sit at room temperature for 1 hr. The catalyst was filtered, rinsed with several 100 ml portions of toluene, and dried under a vacuum.

Example 18

In a 100 ml r.b. flask, 250 mg of triisobutylaluminum was dissolved in 30 ml of toluene. To this solution, 1.00 g. of silica (948 calcined at 300° C.) was added. This slurry was allowed to stand overnight at room temperature. The slurry was filtered through a frit, washed with toluene (3×10 ml) and partially dried under vacuum. In a dried 100 ml r.b. flask, 100 mg of 4,5,6,7-tetrafluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution of (1,3-Me,BuCp)$_2$ZrMe$_2$ in toluene was dissolved in 30 ml of toluene. The partially dried silica was transferred into the flask and the slurry was allowed to stand overnight at room temperature. The slurry was filtered through a frit and dried thoroughly under vacuum.

Example 19

In a 100 ml r.b. flask, 250 mg of triethylaluminum was dissolved in 30 ml of toluene. To this solution, 1.00 g. of silica (948 calcined at 200° C.) was added. This slurry was allowed to stand overnight at room temperature. The slurry was filtered through a frit, washed with toluene (3×10 ml) and partially dried under vacuum. In a dried 100 ml r.b. flask, 200 mg of 5-fluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution of $(1,3\text{-Me,BuCp})_2\text{ZrMe}_2$ in toluene was dissolved in 30 ml of toluene. The partially dried silica was transferred into the flask and the slurry was allowed to stand overnight at room temperature. The slurry was filtered through a frit and dried thoroughly under vacuum.

Example 20

In a 100 ml r.b. flask, 250 mg of triisobutylaluminum was dissolved in 30 ml of toluene. To this solution, 1.00 g. of silica (948 calcined at 200° C.) was added. This slurry was allowed to stand overnight at room temperature. The slurry was filtered through a frit, washed with toluene (3×10 ml) and partially dried under vacuum. In a dried 100 ml r.b. flask, 200 mg of 4,5,6,7-tetrafluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution of $(1,3\text{-Me,BuCp})_2\text{ZrMe}_2$ in toluene was dissolved in 30 ml of toluene. The partially dried silica was transferred into the flask and the slurry was allowed to stand overnight at room temperature. The slurry was filtered through a frit and dried thoroughly under vacuum.

Example 21

In a 100 ml r.b. flask, 250 mg of triisobutylaluminum was dissolved in 30 ml of toluene. To this solution, 1.00 g. of silica (948 calcined at 200° C.) was added. This slurry was allowed to stand overnight at room temperature. The slurry was filtered through a frit, washed with toluene (3×10 ml) and partially dried under vacuum. In a dried 100 ml r.b. flask, 100 mg of 4,5,6,7-tetrafluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution of $(1,3\text{-Me,BuCp})_2\text{ZrMe}_2$ in toluene was dissolved in 30 ml of toluene. The partially dried silica was transferred into the flask and the slurry was allowed to stand overnight at room temperature. The slurry was filtered through a frit and dried thoroughly under vacuum.

Example 22

In a 100 ml r.b. flask, 250 mg of triisobutylaluminum was dissolved in 30 ml of toluene. To this solution, 1.00 g. of silica (948 calcined at 300° C.) was added. This slurry was allowed to stand overnight at room temperature. The slurry was filtered through a frit, washed with toluene (3×10 ml) and-partially dried under vacuum. In a dried 100 ml r.b. flask, 200 mg of 4,5,6,7-tetrafluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution of $(1,3\text{-Me,BuCp})_2\text{ZrMe}_2$ in toluene was dissolved in 30 ml of toluene. The partially dried silica was transferred into the flask and the slurry was allowed to stand overnight at room temperature. The slurry was filtered through a frit and dried thoroughly under vacuum.

Example 23

In a 100 ml r.b. flask, 200 mg of 4,5,6,7-tetrafluoroindole was dissolved in 30 ml of o-xylene. To this solution, 1.00 g. of TEA1-treated silica (948 calcined at 600° C.) was added. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution of $(1,3\text{-Me,BuCp})_2\text{ZrMe}_2$ in toluene was dissolved in 30 ml of toluene. The partially dried silica was transferred into the flask and the slurry was allowed to stand overnight at room temperature. The slurry was filtered through a frit and dried thoroughly under vacuum.

Polymerizations

Polymerizations were performed for the catalyst systems prepared in Examples 17–23 utilizing the same procedure as described above for Examples 1–16.

Pertinent data, for the polymers prepared by the catalyst systems of Comparative Example 1 and Examples 17–23, is summarized in Table 2.

TABLE 2

Polymerization Data Utilizing Catalyst Systems of Examples 1 and 17–23

| Catalyst | Comonomer | Incorporation | Average Mw | Average Mn | Average PDI | Yield | Activity (gP/gCat*hr) |
|---|---|---|---|---|---|---|---|
| Comp. 1 | 1 | 3.1 | 424377.6 | 254601 | 1.7 | 0.133 | 649.5 |
| Comp. 1 | 2 | 3.2 | 430953.9 | 263320 | 1.6 | 0.123 | 656.0 |
| Comp. 1 | 3 | 3 | 420634.5 | 272312 | 1.5 | 0.131 | 620.1 |
| | average | 3.1 | 425322 | 263411 | 2 | 0 | 642 |
| | stddev | 0.1 | 5224 | 8856 | 0 | 0 | 19 |
| 17 | 4 | 3.4 | 393658.9 | 224344 | 1.8 | 0.129 | 1249.7 |
| 17 | 5 | 3.5 | 402083 | 239361 | 1.7 | 0.137 | 1304.1 |
| 17 | 6 | 3.3 | 405971.2 | 238928 | 1.7 | 0.136 | 1286.1 |
| | average | 3.4 | 400571 | 234211 | 2 | 0 | 1280 |
| | stddev | 0.1 | 6294 | 8548 | 0 | 0 | 28 |
| 18 | 1 | 3.2 | 476505.8 | 283278 | 1.7 | 0.11 | 577.2 |
| 18 | 2 | 3.2 | 465474.7 | 282325 | 1.6 | 0.115 | 523.8 |
| 18 | 3 | 3.2 | 460351.6 | 276281 | 1.7 | 0.128 | 484.8 |
| | average | 3.2 | 467444 | 280628 | 2 | 0 | 529 |
| | stddev | 0.0 | 8255 | 3795 | 0 | 0 | 46 |
| 19 | 4 | 3 | 478902.2 | 267006 | 1.8 | 0.127 | 696.0 |
| 19 | 5 | 2.9 | 488375.1 | 301026 | 1.6 | 0.118 | 714.8 |
| 19 | 6 | 2.8 | 483302.6 | 294444 | 1.6 | 0.104 | 661.6 |
| | average | 2.9 | 483527 | 287492 | 2 | 0 | 691 |
| | stddev | 0.1 | 4740 | 18044 | 0 | 0 | 27 |
| 20 | 1 | 3.2 | 431988.3 | 263019 | 1.6 | 0.129 | 754.1 |
| 20 | 2 | 3.2 | 445204.4 | 257303 | 1.7 | 0.122 | 680.6 |
| 20 | 3 | 3.3 | 425137.3 | 262249 | 1.6 | 0.131 | 740.1 |
| | average | 3.2 | 434110 | 260857 | 2 | 0 | 725 |
| | stddev | 0.1 | 10200 | 3102 | 0 | 0 | 39 |
| 21 | 4 | 3.1 | 427548.3 | 246446 | 1.7 | 0.127 | 1020.2 |
| 21 | 5 | 3.2 | 441603.3 | 274261 | 1.6 | 0.122 | 962.1 |
| 21 | 6 | 3.2 | 436116.1 | 261730 | 1.7 | 0.121 | 898.7 |
| | average | 3.2 | 435089 | 260812 | 2 | 0 | 960 |
| | stddev | 0.1 | 7084 | 13930 | 0 | 0 | 61 |
| 22 | 1 | 3.1 | 445283.3 | 256377 | 1.7 | 0.123 | 388.9 |
| 22 | 2 | 3.2 | 446511.3 | 258059 | 1.7 | 0.126 | 459.0 |
| 22 | 3 | 3.2 | 429995.3 | 255286 | 1.7 | 0.126 | 455.0 |
| | average | 3.2 | 440597 | 256574 | 2 | 0 | 434 |
| | stddev | 0.1 | 9202 | 1397 | 0 | 0 | 39 |
| 23 | 4 | 3.4 | 406183.4 | 227330 | 1.8 | 0.12 | 381.1 |
| 23 | 5 | | | | | 0.012 | 184.8 |
| 23 | 6 | 3.2 | 431091.8 | 222797 | 1.9 | 0.113 | 312.0 |
| | average | 3.3 | 418638 | 225063 | 2 | 0 | 293 |
| | stddev | 0.1 | 17613 | 3206 | 0 | 0 | 100 |

Example 24

In a 100 ml r.b. flask, 250 mg of triethylaluminum was dissolved in 30 ml of toluene. To this solution, 1.00 g. of silica (948 calcined at 200° C.) was added. This slurry was allowed to stand overnight at room temperature. The slurry was filtered through a frit, washed with toluene (3×10 ml) and partially dried under vacuum. In a dried 100 ml r.b. flask, 100 mg of 5-fluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was removed from the oil bath and allowed to cool to room temperature. The slurry was then filtered, washed with toluene and partially dried under vacuum. In a dried 100 ml r.b. flask, 100 mg of a 20 wt % solution (in toluene) of (1,3-Me,BuCp)$_2$ZrMe$_2$ was dissolved in 30 ml of toluene. The partially dried silica was transferred into the flask and the slurry was allowed to stand overnight at room temperature. The slurry was filtered through a flit and dried thoroughly under vacuum.

Example 25

0.25 grams of triethylaluminum in toluene were combined with 1.0 grams of silica (Davison 948 100° C. vacuum dried) in a 100 flask. The resulting slurry was allowed to sit overnight. The resulting silica was filtered, and rinsed with several 10 ml portions of toluene. 0.1 grams of 4,5,6,7-tetrafluoroindole was added to silica, slurried in o-xylene and heated to 140° C. for three hours. Over the three hour period, the color of the slurry darkened to an orange and finally a dark orange/brown hue. The silica was then filtered, rinsed with several 10 ml portions of toluene, and subsequently combined with 0.09 grams of a 20 wt % solution of (1,3-Me,BuCp)$_2$ZrMe$_2$ in toluene. The supported catalyst was allowed to sit at room temperature for 1 hr. The catalyst was filtered, rinsed with several 10 ml portions of toluene, and dried under a vacuum.

Example 26

0.35 grams of triethylaluminum in toluene were combined with 1.0 grams of silica (Davison 948) in a 100 flask. The resulting slurry was allowed to sit overnight. The resulting silica was filtered, and rinsed with several 10 ml portions of toluene. 0.1 grams of 5-fluoroindole was added to silica, slurried in o-xylene and heated to 140° C. for three hours. Over the three hour period, the color of the slurry darkened to an orange and finally a dark orange/brown hue. The silica was then filtered, rinsed with several 10 ml portions of toluene, and subsequently combined with 0.09 grams of a 20 wt % solution of (1,3-Me,BuCp)$_2$ZrMe$_2$ in toluene. The supported catalyst was allowed to sit at room temperature for 1 hr. The catalyst was filtered, rinsed with several 10 ml portions of toluene, and dried under a vacuum.

Example 27

0.25 grams of triethylaluminum in toluene were combined with 1.0 grams of silica (Davison 948 100° C. vacuum dried) in a 100 flask. The resulting slurry was allowed to sit overnight. The resulting silica was filtered, and rinsed with several 10 ml portions of toluene. 0.1 grams of indole was added to silica, slurried in o-xylene and heated to 140° C. for three hours. Over the three hour period, the color of the slurry darkened to an orange and finally a dark orange/brown hue. The silica was then filtered, rinsed with several 10 ml portions of toluene, and subsequently combined with 0.09 grams of a 20 wt % solution of $(1,3\text{-Me,BuCp})_2\text{ZrMe}_2$ in toluene. The supported catalyst was allowed to sit at room temperature for 1 hr. The catalyst was filtered, rinsed with several 10 ml portions of toluene, and dried under a vacuum.

Example 28

0.35 grams of triethylaluminum in toluene were combined with 1.0 grams of silica (Davison 948) in a 100 flask. The resulting slurry was heated to 140° C. for three hours. The silica was filtered, and rinsed with several 10 ml portions of toluene. 0.1 grams of 5-fluoroindole was added to silica, slurried in o-xylene and heated to 140° C. for three hours. Over the three hour period, the color of the slurry darkened to an orange and finally a dark orange/brown hue. The silica was then filtered, rinsed with several 10 ml portions of toluene, and subsequently combined with 0.09 grams of a 20 wt % solution of $(1,3\text{-Me,BuCp})_2\text{ZrMe}_2$ in toluene. The supported catalyst was allowed to sit at room temperature for 1 hr. The catalyst was filtered, rinsed with several 10 ml portions of toluene, and dried under a vacuum.

Example 29

In a 100 ml r.b. flask, 250 mg of triethylaluminum was dissolved in 30 ml of toluene. To this solution, 1.00 g. of silica (948 calcined at 200° C.) was added. This slurry was allowed to stand overnight at room temperature. The slurry was filtered through a frit, washed with toluene (3×10 ml) and partially dried under vacuum. In a dried 100 ml r.b. flask, 200 mg of 5-fluoroindole was dissolved in 30 ml of o-xylene. The partially dried silica was transferred to the flask and slurried. An immediate, noticeable color change was observed from the off-white silica to a yellow-tinted slurry. The flask was placed in an oil bath at 140° C. for three hours and stirred every half-hour. Over the three hour period, the color of the slurry darkened to an orange and finally a dark orange/brown hue. The flask was remove from the oil bath and allowed to cool to room temperature. The slurry was then filtered, washed with toluene and partially dried under vacuum. In a dried 100 ml r.b. flask, 100 mg of a 20 wt % solution of (1,3-Me,BuCp)2ZrMe2 in toluene was dissolved in 30 ml of toluene. The partially dried silica was transferred into the flask and the slurry was allowed to stand overnight at room temperature. The slurry was filtered through a flit and dried thoroughly under vacuum.

Example 30

10.0 grams of triethylaluminum in toluene were combined with 40.0 grams of silica (Davison 948 200° C.) in a 100 flask. The resulting slurry was allowed to sit overnight. The resulting silica was filtered, and rinsed with several 100 ml portions of toluene. 4.0 grams of 4,5,6,7-tetrafluoroindole was added to silica, slurried in o-xylene and heated to 140° C. for three hours. Over the three hour period, the color of the slurry darkened to an orange and finally a dark orange/brown hue. The silica was then filtered, rinsed with several 100 ml portions of toluene, and dried under vacuum. 36.0 grams of the support was combined with 2.7 grams of a 20 wt % solution of $(1,3\text{-Me,BuCp})_2\text{ZrMe}_2$ in toluene. The supported catalyst was allowed to sit at room temperature for 1 hr. The catalyst was filtered, rinsed with several 100 ml portions of toluene, and dried under a vacuum.

Example 31

10.0 grams of triethylaluminum in toluene were combined with 40.0 grams of silica (Davison 948 calcined @ 200 ° C.) in a 100 flask. The resulting slurry sat overnight. The silica was filtered, and rinsed with several 100 ml portions of toluene. 4.0 grams of 5-fluoroindole was added to silica, slurried in o-xylene and heated to 140° C. for three hours. Over the three hour period, the color of the slurry became yellow. The silica was then filtered, rinsed with several 100 ml portions of toluene, and dried under vacuum 36.0 grams of this support was combined with 2.6 grams of a 20 wt % solution of $(1,3\text{-Me,BuCp})_2\text{ZrMe}_2$ in toluene. The supported catalyst was allowed to sit at room temperature for 1 hr. The catalyst was filtered, rinsed with several 100 ml portions of toluene, and dried under a vacuum.

Example 32

In a 100 ml r.b. flask, 150 mg of indole was dissolved in 30 ml of o-xylene. 1.00 g of dried silica (146A) was transferred to the flask and slurried. No color change was observed. The flask was placed in an oil bath at 140° C. for three hours and stirred every half-hour. No color change was observed over this period. The flask was removed from the oil bath and allowed to cool to room temperature. The slurry was then filtered, washed with toluene and partially dried under vacuum. In a dried 100 ml r.b. flask, 100 mg of a 20 wt % solution (in toluene) of $(1,3\text{-Me,BuCp})_2\text{ZrMe}_2$ was dissolved in 30 ml of toluene. The partially dried silica was transferred into the flask and the slurry was allowed to stand overnight at room temperature. The slurry was filtered through a frit and dried thoroughly under vacuum.

Example 33

In a 100 ml r.b. flask, 150 mg of 4,5,6,7-tetrafluoroindole was dissolved in 30 ml of o-xylene. 1.00 g of dried silica (146A) was transferred to the flask and slurried. An immediate, noticeable color change was observed from the off-white silica to a yellow-tinted slurry. The flask was placed in an oil bath at 100° C. for three hours and stirred every half-hour. Over the three hour period, the color of the slurry darkened slightly to a yellow-orange color. The flask was remove from the oil bath and allowed to cool to room temperature. The slurry was then filtered, washed with toluene and partially dried under vacuum. In a dried 100 ml r.b. flask, 100 mg of a 20 wt % solution (in toluene) of $(1,3\text{-Me,BuCp})_2\text{ZrMe}_2$ was dissolved in 30 ml of toluene. The partially dried silica was transferred into the flask and the slurry was allowed to stand overnight at room temperature. The slurry was filtered through a frit and dried thoroughly under vacuum.

Example 34

In a 100 ml r.b. flask, 150 mg of 4,5,6,7-tetrafluoroindole was dissolved in 30 ml of o-xylene. 1.00 g of dried silica (146A) was transferred to the flask and slurried. An immediate, noticeable color change was observed from the off-white silica to a yellow-tinted slurry. The flask was placed in an oil bath at 120° C. for three hours and stirred every half-hour. Over the three hour period, the color of the slurry darkened slightly to a orange-yellow color. The flask was remove from the oil bath and allowed to cool to room temperature. The slurry was then filtered, washed with toluene and partially dried under vacuum. In a dried 100 ml r.b. flask, 100 mg of a 20 wt % solution (in toluene) of (1,3-Me,BuCp)$_2$ZrMe$_2$ was dissolved in 30 ml of toluene. The partially dried silica was transferred into the flask and the slurry was allowed to stand overnight at room temperature. The slurry was filtered through a frit and dried thoroughly under vacuum.

Example 35

0.25 grams of triethylaluminum in toluene were combined with 1.0 grams of silica (Davison 948 100° C. vacuum dried) in a 100 flask. The resulting slurry was allowed to sit overnight. The resulting silica was filtered, and rinsed with several 10 ml portions of toluene. 0.1 grams of 5-fluoroindole was added to silica, slurried in o-xylene and heated to 140° C. for three hours. Over the three hour period, the color of the slurry darkened to an orange and finally a dark orange/brown hue. The silica was then filtered, rinsed with several 10 ml portions of toluene, and subsequently combined with 0.09 grams of a 20 wt % solution of (1,3-Me,BuCp)$_2$ZrMe$_2$ in toluene. The supported catalyst was allowed to sit at room temperature for 1 hr. The catalyst was filtered, rinsed with several 10 ml portions of toluene, and dried under a vacuum.

Example 36

In a 100 ml r.b. flask, 1.00 g of triethylaluminum was dissolved in 60 ml of toluene. To this solution, 5.00 g. of silica (948 calcined at 200° C.) was added. This slurry was allowed to stand overnight at room temperature. The slurry was filtered through a frit, washed with toluene (3×10 ml), dried throughly under vacuum and labeled 146A. In a dried 100 ml r.b. flask, 150 mg of 4,5,6,7-tetrafluoroindole was dissolved in 30 ml of o-xylene. 1.00 g of dried silica (146A) was transferred to the flask and slurried. An immediate, noticeable color change was observed from the off-white silica to a yellow-tinted slurry. The flask was placed in an oil bath at 85° C. for three hours and stirred every half-hour. Over the three hour period, the color of the slurry darkened very slightly. The flask was remove from the oil bath and allowed to cool to room temperature. The slurry was then filtered, washed with toluene and partially dried under vacuum. In a dried 100 ml r.b. flask, 100 mg of a 20 wt % solution (in toluene) of (1,3-Me,BuCp)$_2$ZrMe$_2$ was dissolved in 30 ml of toluene. The partially dried silica was transferred into the flask and the slurry was allowed to stand overnight at room temperature.

Example 37

In a 100 ml r.b. flask, 150 mg of 4,5,6,7-tetrafluoroindole was dissolved in 30 ml of o-xylene. 1.00 g of dried silica (146A) was transferred to the flask and slurried. An immediate, noticeable color change was observed from the off-white silica to a yellow-tinted slurry. The flask was left at room temperature over three days The color of the slurry stayed light in color. The slurry was then filtered, washed with toluene and partially dried under vacuum. In a dried 100 ml r.b. flask, 100 mg of a 20 wt % solution (in toluene) of (1,3-Me,BuCp)$_2$ZrMe$_2$ was dissolved in 30 ml of toluene. The partially dried silica was transferred into the flask and the slurry was allowed to stand overnight at room temperature. The slurry was filtered through a frit and dried thoroughly under vacuum.

Polymerizations

Polymerizations were performed for the catalyst systems prepared in Examples 24–37 utilizing the same procedure as described above for Examples 1–16.

Pertinent data, for the polymers prepared by the catalyst systems of Comparative Example 1 and Examples 24–37, is summarized in Table 3.

TABLE 3

Polymerization Data Utilizing Catalyst Systems of Examples 1 and 24–37

| Catalyst | Comonomer Incorporation | Average Mw | Average Mn | Average PDI | Yield | Activity (gP/gCat*hr) |
|---|---|---|---|---|---|---|
| Comp. 1 | 1 | 2.8 | 380220.2 | 219893 | 1.7 | 0.13 | 475.1 |
| Comp. 1 | 2 | 2.8 | 376394.7 | 220195 | 1.7 | 0.13 | 608.4 |
| Comp. 1 | 3 | 2.8 | 388153.5 | 225242 | 1.7 | 0.13 | 579.9 |
| | average | 2.8 | 381589 | 221777 | 2 | 0 | 554 |
| | stddev | 0.0 | 5998 | 3005 | 0 | 0 | 70 |
| 24 | 4 | 2.7 | 434129.6 | 254931 | 1.7 | 0.095 | 295.7 |
| 24 | 5 | 2.6 | 437231.6 | 246525 | 1.8 | 0.118 | 428.4 |
| 24 | 6 | 2.9 | 432701 | 261855 | 1.7 | 0.124 | 606.4 |
| | average | 2.7 | 434687 | 254437 | 2 | 0 | 443 |
| | stddev | 0.2 | 2316 | 7677 | 0 | 0 | 156 |
| 25 | 1 | 3.1 | 358356.7 | 199537 | 1.8 | 0.141 | 1480.9 |
| 25 | 2 | 3.3 | 347803.9 | 195597 | 1.8 | 0.138 | 1274.5 |
| 25 | 3 | 3.2 | 353588.5 | 197912 | 1.8 | 0.139 | 1368.8 |
| | average | 3.2 | 353250 | 197682 | 2 | 0 | 1375 |
| | stddev | 0.1 | 5285 | 1980 | 0 | 0 | 103 |
| 26 | 4 | 2.9 | 410401.7 | 233119 | 1.8 | 0.113 | 589.4 |
| 26 | 5 | 2.9 | 425087.1 | 258169 | 1.6 | 0.129 | 748.5 |
| 26 | 6 | 2.9 | 404252.5 | 226393 | 1.8 | 0.128 | 707.2 |
| | average | 2.9 | 413247 | 239227 | 2 | 0 | 682 |
| | stddev | 0.0 | 10705 | 16746 | 0 | 0 | 83 |
| 27 | 1 | 3 | 419632.8 | 249435 | 1.7 | 0.11 | 432.1 |
| 27 | 2 | 2.8 | 442742 | 268179 | 1.7 | 0.058 | 344.9 |

TABLE 3-continued

Polymerization Data Utilizing Catalyst Systems of Examples 1 and 24–37

| Catalyst | Comonomer Incorporation | Average Mw | Average Mn | Average PDI | Yield | Activity (gP/gCat*hr) |
|---|---|---|---|---|---|---|
| 27 | 3 | 2.9 | 446808.5 | 261866 | 1.7 | 0.124 | 336.5 |
|  | average | 2.9 | 436394 | 259827 | 2 | 0 | 371 |
|  | stddev | 0.1 | 14658 | 9537 | 0 | 0 | 53 |
| 28 | 4 | 3 | 390819.8 | 231964 | 1.7 | 0.123 | 855.2 |
| 28 | 5 | 3 | 409805 | 237484 | 1.7 | 0.132 | 931.7 |
| 28 | 6 | 2.8 | 343700 | 200670 | 1.7 | 0.12 | 1021.8 |
|  | average | 2.9 | 381442 | 223373 | 2 | 0 | 936 |
|  | stddev | 0.1 | 34036 | 19854 | 0 | 0 | 83 |
| 29 | 1 | 3 | 443182 | 253052 | 1.8 | 0.125 | 557.4 |
| 29 | 2 | 2.8 | 439174.3 | 252634 | 1.7 | 0.119 | 614.0 |
| 29 | 3 | 2.9 | 449515 | 266835 | 1.7 | 0.127 | 611.2 |
|  | average | 2.9 | 443957 | 257507 | 2 | 0 | 594 |
|  | stddev | 0.1 | 5214 | 8081 | 0 | 0 | 32 |
| 30 | 4 | 3.1 | 378248.8 | 225857 | 1.7 | 0.123 | 767.6 |
| 30 | 5 | 3.3 | 382525.6 | 224916 | 1.7 | 0.132 | 1066.7 |
| 30 | 6 | 3.2 | 376774.8 | 227907 | 1.7 | 0.128 | 998.9 |
|  | average | 3.2 | 379183 | 226227 | 2 | 0 | 944 |
|  | stddev | 0.1 | 2987 | 1529 | 0 | 0 | 157 |
| 31 | 4 | 2.9 | 402834.2 | 238283 | 1.7 | 0.121 | 826.2 |
| 31 | 5 | 2.8 | 418415.6 | 241266 | 1.7 | 0.125 | 815.3 |
| 31 | 6 | 2.9 | 404376 | 226705 | 1.8 | 0.12 | 794.7 |
|  | average | 2.9 | 408542 | 235418 | 2 | 0 | 812 |
|  | stddev | 0.1 | 8586 | 7691 | 0 | 0 | 16 |
| 32 | 1 | 2.6 | 492528.8 | 289158 | 1.7 | 0.063 | 140.0 |
| 32 | 2 | 2.8 | 541200.6 | 317437 | 1.7 | 0.065 | 144.4 |
| 32 | 3 | 2.7 | 537768 | 315793 | 1.7 | 0.067 | 148.9 |
|  | average | 2.7 | 523832 | 307463 | 2 | 0 | 144 |
|  | stddev | 0.1 | 27164 | 15874 | 0 | 0 | 4 |
| 33 | 4 | 3.4 | 362652.7 | 207934 | 1.7 | 0.137 | 1461.1 |
| 33 | 5 | 3.3 | 360424.4 | 202956 | 1.8 | 0.137 | 1453.0 |
| 33 | 6 | 3.1 | 365856.1 | 211387 | 1.7 | 0.141 | 1710.9 |
|  | average | 3.3 | 362978 | 207426 | 2 | 0 | 1542 |
|  | stddev | 0.2 | 2730 | 4238 | 0 | 0 | 147 |
| 34 | 1 | 3.5 | 358544.4 | 207545 | 1.7 | 0.141 | 1446.3 |
| 34 | 2 | 3.4 | 347409.8 | 197193 | 1.8 | 0.14 | 1480.3 |
| 34 | 3 | 3.5 | 353951.7 | 200281 | 1.8 | 0.142 | 1457.9 |
|  | average | 3.5 | 353302 | 201673 | 2 | 0 | 1462 |
|  | stddev | 0.1 | 5596 | 5314 | 0 | 0 | 17 |
| 35 | 4 | 3.6 | 388779.6 | 211955 | 1.8 | 0.129 | 846.4 |
| 35 | 5 | 3.3 | 406451.5 | 254636 | 1.6 | 0.12 | 841.2 |
| 35 | 6 | 3 | 399957.7 | 225841 | 1.8 | 0.129 | 821.5 |
|  | average | 3.3 | 398396 | 230811 | 2 | 0 | 836 |
|  | stddev | 0.3 | 8939 | 21770 | 0 | 0 | 13 |
| 36 | 1 | 3.6 | 376244.7 | 221747 | 1.7 | 0.135 | 1014.6 |
| 36 | 2 | 3.4 | 373889.1 | 211149 | 1.8 | 0.133 | 989.0 |
| 36 | 3 | 3.3 | 376539.5 | 216765 | 1.7 | 0.133 | 916.1 |
|  | average | 3.4 | 375558 | 216554 | 2 | 0 | 973 |
|  | stddev | 0.2 | 1453 | 5302 | 0 | 0 | 51 |
| 37 | 4 | 3.2 | 362077.3 | 205626 | 1.8 | 0.13 | 964.1 |
| 37 | 5 | 3.2 | 370946.3 | 213202 | 1.7 | 0.133 | 1180.4 |
| 37 | 6 | 3.2 | 372298.1 | 216401 | 1.7 | 0.134 | 1202.5 |
|  | average | 3.2 | 368441 | 211743 | 2 | 0 | 1116 |
|  | stddev | 0.0 | 5552 | 5534 | 0 | 0 | 132 |

We claim:

1. A polymerization process comprising combining ethylene, at least one $C_4$ to $C_{12}$ α-olefin and a catalyst system comprising a polymerization catalyst and an activator; wherein the activator comprises a heterocyclic compound, which may be substituted or unsubstituted, in combination with an aluminum containing compound; wherein the aluminum containing compound is an alumoxane or an alkylaluminum compound represented by the formula $AlR_3$ wherein each R is independently a substituted or unsubstituted alkyl group.

2. The process of claim 1, further comprising a support material.

3. The process of claim 1, wherein the heterocyclic compound is selected from the group consisting of pyrroles, imidazoles, pyrazoles, pyrrolines, pyrrolidines, purines, carbazoles, indoles, phenyl indoles, 2,5-dimethylpyrroles, 3-pentafluorophenyl pyrrole, 4,5,6,7-tetrafluoroindole, 3,4-difluoropyrroles, and combinations thereof.

4. The process of claim 1, wherein the heterocyclic compound is substituted with one or more substituent groups selected from the group consisting of a halogen atom, and a halogen atom containing group.

5. The process of claim 4, wherein the halogen atom or the halogen atom group comprises chlorine, fluorine or bromine.

6. The process of claim 2, wherein the support material is treated with the alumoxane or the alkylaluminum compound such that the support has aluminum alkyl groups bonded thereto.

7. The process of claim 1, wherein the heterocyclic compound is an indole represented by:

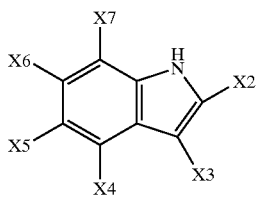

Formula (I)

wherein each of X2 to X7 is independently selected from the group consisting of hydrogen, halogen, an alkyl group, a halogenated or partially halogenated alkyl group, an aryl group, a halogenated or partially halogenated aryl group, an alkoxide group, a halogenated or partially halogenated alkoxide group, an aryloxide group, a halogenated or partially halogenated aryloxide group, an aryl substituted alkyl group, and a halogenated or partially halogenated aryl substituted alkyl group.

8. The process of claim 7, wherein the halogenated or partially halogenated group comprises a chlorine atom, a bromine atom or a fluorine atom.

9. The process of claim 1, wherein the activator is represented one of the following formulae:

   (a.)

or

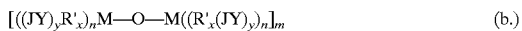   (b.)

or

   (c.)

wherein M is a Group 13 atom;

(JY) represents a substituted or unsubstituted heterocyclic group attached to M, wherein J represents at least one heteroatom contained in the (JY) group;

n is 1 or 2 in formula (a.); n is 2 in formula (b.); and n is a number from 1 to 1000 in formula (c.);

m is a number from 1 to 10;

x+y=the valence of M in formula (a.); x+y=the valence of M−1 in formula (b.); and x+y=valence of M−2 in formula (c.);

each R' is independently a substituted or unsubstituted alkyl group bonded to M.

10. The process of claim 9, wherein J is bonded to M and wherein (JY) is not perhalogenated.

11. The process of claim 9, wherein

M is Al or B; and (JY) is an substituted or unsubstituted indolyl group where the substituents are selected from hydrogen, halogen, an alkyl group, a halogenated or partially halogenated alkyl group, and aryl group, a halogenated or partially halogenated aryl group, an aryl substituted alkyl group, a halogenated or partially halogenated aryl substituted alkyl group.

12. The process of claim 2, wherein the support material is an Group 2, 3, 4, 5, 13 or 14 metal oxide.

13. The process of claim 2, wherein the support is silica.

14. The process of claim 1, wherein the polymerization catalyst is a bulky ligand metallocene catalyst having the formulas:

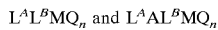

wherein each of $L^A$, $L^B$ and Q are bound to M;

each of $L^A$ and $L^B$ are substituted or unsubstituted cyclopentadienyl ligands or cyclopentadienyl-type ligands;

M is a Group 4, 5 or 6 transition metal;

Q is a leaving group; n is 0, 1 or 2; and

A is a divalent bridging group bound to each of $L^A$ and $L^B$.

15. The process of claim 1, wherein the polymerization process is a gas phase process.

16. The process of claim 1, wherein the polymerization process is a slurry process.

17. The process of claim 15, wherein the reactor temperature ranges from about 60° C. to about 115° C.

18. The process of claim 15, wherein the reactor pressure ranges from 100 psig (690 kPa) to about 500 psig (3448 kPa).

19. The process of claim 15, wherein the reactor pressure ranges from 200 psig (1379 kPa) to about 400 psig (2759 kPa).

20. The polymerization process of claim 1, wherein the catalyst system is combined in a polymerization reactor with the olefins to produce a polyolefin having a melt index ranging from 0.01 to 100 dg/min and a PDI (Mw/Mn) value of greater than 1.5 to 15.

21. A polymerization process comprising combining ethylene, at least one $C_4$ to $C_{12}$ α-olefin and a catalyst system comprising a polymerization catalyst, an inorganic oxide support and an activator; wherein the activator comprises a heterocyclic compound in combination with an alkylaluminum compound represented by the formula $AlR_3$ wherein each R is independently a substituted or unsubstituted alkyl group;

wherein the heterocyclic compound comprising at least one atom selected from Group 15 or 16 of the Periodic Table of Elements; and wherein the polymerization catalyst is selected from bulky ligand metallocene catalysts, Group 15 atom containing polymerization catalyst compounds, and phenoxide transition metal catalyst compositions.

22. The polymerization process of claim 21, wherein the support is selected from silica, fumed silica, alumina, silica-alumina, zeolites and mixtures thereof.

23. The polymerization process of claim 21, wherein the R groups are independently selected from $C_1$ to $C_{30}$ alkyls.

24. The polymerization process of claim 21, wherein the alkylaluminum is selected from trimethylaluminum, triethylaluminum, triisobutylaluminum, tri-n-hexylaluminum, tri-n-octylaluminum, tri-iso-octylaluminum, triphenylaluminum, and combinations thereof.

25. The polymerization process of claim 21, wherein the heterocyclic compound is an indole represented by:

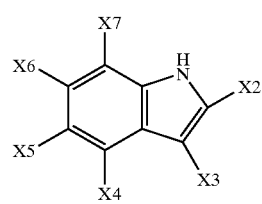

Formula (I)

wherein each of X2 to X7 is independently selected from the group consisting of hydrogen, halogen, an alkyl group, a halogenated or partially halogenated alkyl group, an aryl group, a halogenated or partially halogenated aryl group, an alkoxide group, a halogenated or partially halogenated alkoxide group, an aryloxide group, a halogenated or partially halogenated aryloxide group, an aryl substituted alkyl group, and a halogenated or partially halogenated aryl substituted alkyl group.

26. The polymerization process of claim 25, wherein each of X2 to X7 are independently selected from hydrogen, fluorine, chlorine and bromine.

27. The polymerization process of claim 21, wherein the heterocyclic compound is selected from the group consisting of pyrroles, imidazoles, pyrazoles, pyrrolines, pyrrolidines, purines, carbazoles, indoles, phenyl indoles, 2,5-dimethylpyrroles, 3-pentafluorophenyl pyrrole, 4,5,6,7-tetrafluoroindole, 3,4-difluoropyrroles, and combinations thereof.

28. The polymerization process of claim 21, wherein the polymerization catalyst is a bulky ligand metallocene catalyst having the formulas:

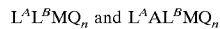

$L^A L^B MQ_n$ and $L^A AL^B MQ_n$ wherein each of $L^A$, $L^B$ and Q are bound to M;
each of $L^A$ and $L^B$ are substituted or unsubstituted cyclopentadienyl ligands or cyclopentadienyl-type ligands;
M is a Group 4, 5 or 6 transition metal;
Q is a leaving group; n is 0, 1 or 2; and
A is a divalent bridging group bound to each of $L^A$ and $L^B$.

29. The polymerization process of claim 28, wherein M is titanium, zirconium or hafnium.

30. The polymerization process of claim 21, further comprising an additional activator selected from aluminoxane, modified aluminoxane, tri(n-butyl)ammonium tetrakis(pentafluorophenyl)boron, trisperfluorophenylboron, trisperfluoronaphthyl boron, polyhalogenated heteroborane anions, tris(2,2',2"-nona-fluorobiphenyl) fluoroaluminate, organo-boron-aluminum compounds, dioctadecylmethylammonium-bis(tris(pentafluorophenyl)borane)benzimidazolide and combinations thereof.

31. The polymerization process of claim 21, wherein the inorganic oxide support is treated with the alkylaluminum compound such that the support has aluminum alkyl groups bonded thereto.

32. The polymerization process of claim 21, wherein the inorganic oxide support and alkylaluminum compound are combined prior to combining the heterocyclic compound.

33. The polymerization process of claim 21, wherein the combination of the heterocyclic compound and the product of the combination of the alkylaluminum and inorganic oxide support is heated.

34. The polymerization process of claim 21, wherein the polymerization process is combined in a polymerization reactor with olefins to produce a polyolefin having a melt index ranging from 0.01 to 100 dg/min and a PDI (Mw/Mn) value of greater than 1.5 to 15; wherein the olefins are ethylene and an olefin selected from $C_4$ to $C_{12}$ olefins.

35. A polymerization process comprising combining ethylene, at least one $C_4$ to $C_2$ α-olefin and a supported polymerization process; the supported polymerization process prepared by combining a heterocyclic compound with an aluminoxane or an alkylaluminum compound with a support material such that the support material contains aluminum alkyl groups bonded thereto.

36. The process of claim 35, wherein the heterocyclic compound is an indole represented by:

Formula (I)

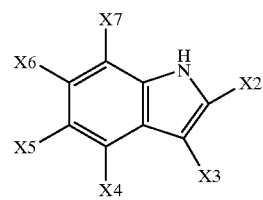

wherein each of X2 to X7 is independently selected from the group consisting of hydrogen, halogen, an alkyl group, a halogenated or partially halogenated alkyl group, an aryl group, a halogenated or partially halogenated aryl group, an alkoxide group, a halogenated or partially halogenated alkoxide group, an aryloxide group, a halogenated or partially halogenated aryloxide group, an aryl substituted alkyl group, and a halogenated or partially halogenated aryl substituted alkyl group.

37. The process of claim 35, further comprising a support material.

38. The process of claim 35, wherein the aluminum containing compound is an alumoxane or an aluminum alkyl compound represented by the formula $AlR_3$ wherein each R is independently a substituted or unsubstituted alkyl group or a substituted or unsubstituted aryl group.

39. The process of claim 35, wherein the aluminum containing compound is an alumoxane or an aluminum alkyl compound represented by the formula $AlR_3$ wherein each R is independently a substituted or unsubstituted alkyl group.

40. The process of claim 35, wherein the heterocyclic compound is selected from the group consisting of pyrroles, imidazoles, pyrazoles, pyrrolines, pyrrolidines, purines, carbazoles, indoles, phenyl indoles, 2,5-dimethylpyrroles, 3-pentafluorophenyl pyrrole, 4,5,6,7-tetrafluoroindole, 3,4-difluoropyrroles, and combinations thereof.

41. The process of claim 35, wherein the heterocyclic compound is substituted with one or more substituent groups selected from the group consisting of a halogen atom, and a halogen atom containing group.

42. The process of claim 41, wherein the halogen atom or the halogen atom group comprises chlorine, fluorine or bromine.

43. The process of claim 42, wherein the support material is treated with the alumoxane or the alkylaluminum compound such that the support has aluminum alkyl groups bonded thereto.

* * * * *